United States Patent
Tang

(10) Patent No.: US 8,718,944 B2
(45) Date of Patent: May 6, 2014

(54) PATIENT-SPECIFIC IMAGE-BASED COMPUTATIONAL MODELING AND TECHNIQUES FOR HUMAN HEART SURGERY OPTIMIZATION

(75) Inventor: Dalin Tang, Shrewsbury, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 1440 days.

(21) Appl. No.: 12/125,366

(22) Filed: May 22, 2008

(65) Prior Publication Data

US 2008/0319308 A1 Dec. 25, 2008

Related U.S. Application Data

(60) Provisional application No. 60/931,282, filed on May 22, 2007.

(51) Int. Cl.
| | |
|---|---|
| *G06F 19/00* | (2011.01) |
| *G06K 9/00* | (2006.01) |
| *G06K 9/20* | (2006.01) |
| *G06K 9/36* | (2006.01) |
| *A61B 5/02* | (2006.01) |

(52) U.S. Cl.
USPC .............. 702/19; 600/508; 600/481; 382/128; 382/282; 382/286

(58) Field of Classification Search
USPC ......... 600/439, 450, 416, 509, 508, 529, 407, 600/481; 382/128, 282, 286; 128/661; 364/413.03; 702/19
See application file for complete search history.

(56) References Cited

U.S. PATENT DOCUMENTS

| | | |
|---|---|---|
| 7,751,984 B2 | 7/2010 | Tang |
| 8,554,490 B2 | 10/2013 | Tang et al. |

(Continued)

FOREIGN PATENT DOCUMENTS

| | | |
|---|---|---|
| WO | WO 2006/062958 A2 | 6/2006 |
| WO | WO 2010/099016 A1 | 9/2010 |

OTHER PUBLICATIONS

Axel, Leon, "Biomechanical Dynamics of the Heart with MRI", *Annu. Rev. Biomed. Eng.*, vol. 4, Annual Reviews, pp. 321-347, 2002.

(Continued)

*Primary Examiner* — Elmer Chao
(74) *Attorney, Agent, or Firm* — Hamilton, Brook, Smith & Reynolds, P.C.

(57) ABSTRACT

A method for determining cardiac status comprises for a given patient, constructing a patient-specific, three-dimensional, computational model of the patient's heart; and executing the constructed computational model, said executing generating a quantitative analysis of cardiac function. A method of performing cardiac surgeries comprises: a) assessing surgical options based on a patient-specific, three-dimensional, computational model of a patient's heart; and b) performing surgery based on one or more of the surgical options. A computer system comprises: a) a data source containing data of a patient's heart; b) a modeler coupled to receive data from the data source, the modeler generating a patient-specific, three-dimensional, computational model of the heart based on the heart data; and c) a processor routine for computationally providing information about a certain cardiac function using the three-dimensional heart model and for applying computational, quantitative analysis of the cardiac function, wherein the quantitative analysis of the cardiac function provides an assessment for surgical options, optimizing surgical techniques, or predicting outcomes.

31 Claims, 32 Drawing Sheets

(56) References Cited

U.S. PATENT DOCUMENTS

| | | | |
|---|---|---|---|
| 2002/0035459 A1* | 3/2002 | Grass et al. | 703/11 |
| 2004/0153128 A1* | 8/2004 | Suresh et al. | 607/14 |
| 2005/0187461 A1* | 8/2005 | Murphy et al. | 600/416 |
| 2006/0149522 A1 | 7/2006 | Tang | |
| 2008/0228086 A1 | 9/2008 | Ilegbusi et al. | |
| 2011/0295579 A1 | 12/2011 | Tang | |

OTHER PUBLICATIONS

Bathe, Klaus-Jürgen, "Finite element developments for general fluid flows with structural interactions", *Internal Journal for Numerical Methods in Engineering*, vol. 60, John Wiley & Sons, Ltd., pp. 213-232, 2004.

Bloomgarden, Daniel C., "Global Cardiac Function using Fast Breath-hold MRI: Validation of New Acquisition and Analysis Techniques", Williams & Wilkins, pp. 683-692, 1997.

Costa, Kevin D., et al., "Laminar fiber architecture and three-dimensional systolic mechanics in canine ventricular myocardium", American Physiological Society, pp. H595-H607, 1999.

Dang, Alan B.C., et al., "Effect of Ventricular Size and Patch Stiffness in Surgical Anterior Ventricular Restoration: A Finite Element Model Study", *The Society of Thoracic Surgeons*, vol. 79, Elsevier Inc., pp. 185-193, 2005.

Nido, Pedro J. del, "Surgical Management of Right Ventricular Dysfunction Late After Repair of Tetralogy of Fallot: Right Ventricular Remodeling Surgery", *Pediatric Cardiac Surgery Annual*, Elsevier Inc., pp. 1-6, 2006.

Geva, Tal, et al., "Evaluation of Regional Differences in Right Ventricular Systolic Function by Acoustic Quantification Echocardiography and Cine Magnetic Resonance Imaging", *Circulation*, vol. 98, American Heart Association, pp. 339-345, 1998.

Geva, Tal, et al., "Gadolinium-Enhanced 3-Dimensional Magnetic Resonsance Angiography of Pulmonary Blood Supply in Patients With Complex Pulmonary Stenosis or Atresia: Comparison With X-Ray Angiography", *Circulation*, vol. 106, American Heart Association, pp. 473-478, 2002.

Geva, Tal, et al., "Factors Associated With Impaired Clinical Status in Long-Term Survivors of Tetralogy of Fallot Repair Evaluated by Magnetic Resonance Imagining", *Circulation*, vol. 43, No. 6, Journal of the American Collage of Cardiology, pp. 1068-1074, 2004.

Guccione, J.M., et al., "Mechanics of Active Contraction in Cardiac Muscle: Part I—Constitutive Relations for Fiber Stress That Describe Deactivation", *Journal of Biomechanical Engineering*, vol. 115, pp. 72-81, 1993.

Guccione, J.M., et al., "Measurements of Active Myocardial Tension Under a Wide Range of Physiological Loading Conditions", *J. Biomechanics*, vol. 30, No. 2, Elsevier Science Ltd., pp. 189-192, 1997.

Guccione, Julius M., et al., "Finite Element Stress Analysis of Left Ventricular Mechanics in the Beating Dog Heart", *J. Biomechanics*, vol. 28, No. 10, Elsevier Science Ltd., pp. 1167-1177, 1995.

Guccione, J.M., et al., "Passive Material Properties of Intact Ventricular Myocardium Determined From a Cylindrical Model", *Journal of Biomechanical Engineering*, vol. 113, pp. 42-55, 1991.

Guccione, J.M., et al., "Mechanics of Active Contraction in Cardiac Muscle: Part II—Cylindrical Models of the Systolic Left Ventricle", *Journal of Biomechanical Engineering*, vol. 115, pp. 82-90, 1993.

Holzapfel, Gerhard A., et al., "A Layer-Specific Three-Dimensional Model for the Simulation of Balloon Angioplasty using Magnetic Resonance Imaging and Mechanical Testing", *Annals of Biomedical Engineering*, vol. 30, Biomedical Engineering Society, pp. 753-767, 2002.

Holzapfel, Gerhard A., et al., "A New Constitutive Framework for Arterial Wall Mechanics and a Comparative Study of Material Models", *Journal of Elasticity*, vol. 61, pp. 1-48, 2000.

Holzapfel, Gerhard A., et al., "A Layer-Specific Three Dimensional Model for the Simulation of Balloon Antioplasty using Magnetic Resonance Imaging and Mechanical Testing", *Annals of Biomedical Engineering*, vol. 30, pp. 753-767, 2002.

Hunter, Peter, J., "Modeling Total Heart Function", *Annu. Rev. BiomedEng.*, vol. 5, pp. 147-177, 2003.

Kuehne, T., et al., "Magnetic Resonance Imaging Analysis of Right Ventricular Pressure-Volume Loops: In Vivo Validation and Clinical Application in Patients with Pulmonary Hypertension", *circ. ahajournals.org at Harvard University*, Downloaded on May 18, 2008.

May-Newman, Karen, et al., "Homogenization Modeling for the Mechanics of Perfused Myocardium", *Progress in Biophysics & Molecular Biology*, vol. 69, pp. 463-481, 1998.

McCulloch, Andrew, et al., "Large-Scale Finite Element Analysis of the Beating Hart", *Critical Reviews in Biomedical Engineering*, vol. 20, No. 5, 6, pp. 427-449, 1992.

Metaxas, Dimitris, N., et al., "Three-Dimiensional Motion Reconstruction and Analysis of the right Ventricle from Planar Tagged MRI", *UMI Microform* 9965488, pp. i-xvii and 1-114, 2000.

Nash, M. P., et al., "Computational Mechanics of the Heart", *Journal of Elasticity*, vol. 61, pp. 113-141, 2000.

Peskin, Charles S., et al., "Cardiac Fluid Dynamics", *Critical Reviews in Biomedical Engineering*, vol. 20, No. 5,6, pp. 451-459, 1992.

Rogers, Jack M., et al., "Nonuniform Muscle Fiber Orientation Causes Spiral Wave Drift in a Finite Element Model of Cardiac Action Potential Propagation", *J Cardiovasc Electrophysiol*, vol. 5, pp. 496-509, 1994.

Sanchez-Quintana, D., et al., "Ventricular Myoarchitecture in Tetralogy of Fallot", *Heart*, vol. 76, pp. 280-286, 1996.

Stevens, Carey, et al., "Sarcomere Length Changes in a 3D Mathematical Model of the Pig Ventricles", *Progress in Biophysics & Molecular Biology*, vol. 82, pp. 229-241, 2003.

Stevens, Carey, et al., "Ventricular Mechanics in Diastole: Material Parameter Sensitivity", *Journal of Biomechanics*, vol. 36, pp. 737-748, 2003.

Yakayama, Yasuo, et al., "Contribution of Laminar Myofiber Architecture to Load-Dependent Changes in Mechanics of LV Myocardium", *Am J Physiol Hear Circ Physiol*, vol. 282, pp. H1510-1520, 2002.

Tang, Dalin, et al., "Effect of Stenosis Asymmetry on Blood Flow and Artery Compression: A Three-Dimensional Fluid-Structure Interaction Model", *Annals of Biomedical Engineering*, vol. 31, pp. 1182-1193, 2003.

Tang, Dalin, et al., "3D MRI-Based Multicomponent FSI Models for Atherosclerotic Plaques", *Annals of Biomedical Engineering*, vol. 32, No. 7, 2004.

Tang, Dalin, et al., "Local Maximal Stress Hypothesis and Computational Plaque Vulnerability Index for Atherosclerotic Plaque Assessment", *Annals of Biomedical Engineering*, vol. 33, No. 12, pp. 1789-1801, 2005.

Tang, D., et al., "Image-Based RV/LV Combination Structure-only and FSI Models for Mechanical Analysis of Human Right Ventricle Remodeling Surgery Design"; *Journal of Biomechanics*, vol. 39 (Suppl 1), p. S438, 2006. (Oral Presentations).

Tang, Dalin, et al., "Effect of a Lipid Pool on Stress/Strain Distributions in Stenotic Arteries: 3-D Fluid-Structure Interactions (FSI) Models", *Journal of Biomechanical Engineering*, vol. 126, pp. 363-370, 2004.

Therrien, Judith, "Pulmonary Volve Replacement in Adults Late After Repair of Tetralogy of Fallot: Are We Operating Too Late?", *Journal of the Americal College of Cardiology*, vol. 36, No. 5, pp. 1670-1675, 2000.

Usyk, Taras, et al., "Three Dimensional Electromechanical Model of Porcine Heart with Penetrating Wound Injury", *Medicine Meets Virtual Reality*, vol. 13, pp. 568-573, 2005.

Vetter, Frederick J., et al., "Three-Dimensional Analysis of Regional Cardiac Function: a Model of Rabbit Ventricular Anatomy", *Progress in Biophysics & Molecular Biology*, No. 69, pp. 157-183 (1998).

Vetter, Frederick J., et al., "Three-Dimensional Stress and Strain in Passive Rabbit Left Ventricle: A Model Study", *Annals of Biomedical Engineering*, vol. 28, pp. 781-792, 2000.

Vliegen, Hubert W., et al., "Magnetic Resonance Imaging to Assess the Hemodynamic Effects of Pulmonary Valve Replacement in Adults Late After Repair of Tetralogy of Fallot", *circ.ahajournals. org at Harvard University*, pp. 1704-1707, 2008.

(56) References Cited

OTHER PUBLICATIONS

Waien, Sohail, A., "Serial Follow-Up of Adults with Repaired Tetralogy of Fallot", *JACC*, vol. 20, No. 2, pp. 295-300, 1992.

Yang, Chun, et al., "In Vivo MRI-Based 3D FSI RV/LV Models for Human Right Ventricle and Patch Design for Potential Computer-Aided Surgery Optimization", *Computers and Structures*, vol. 85, pp. 988-997, 2007.

Rekhter, M.D., et al., "Hypercholesterolemia Causes Mechanical Weakening of Rabbit Atheroma," *Circ. Res.*, 86:101-108 (2000) (month not available).

International Search Report from International Application No. PCT/US2005/044085, mailed on Jul. 27, 2006.

International Preliminary Report on Patentability from International Application No. PCT/US2005/044085, mailed on Jun. 13, 2007.

International Search Report from International Application No. PCT/US2010/024527, mailed on Apr. 29, 2010.

International Preliminary Report on Patentability from International Application No. PCT/US2010/024527, mailed on Aug. 30, 2011.

Lee, K.W. et al., "Ultrasound image-based computer model of a common carotid artery with a plague," *Medical Engineering & Physics* 26(823-840), 2004.

Gerbeau, Jean-Frederic, et al., "Fluid-Structure Interaction in Blood Flows on Geometries coming from Medical Imaging," *Rapports de Recherche No. 5052*, Dec. 2003 (retrieved from the Internet: URL: http://www.ann.jussieu.fr/{frey/publications/RR-5052.pdf, Retrieved Jul. 10, 2006).

Huang, X.. et al., "Patient-Specific Artery Shrinkage and 3D Zero-Stress State in Multi-Component 3D FSI Models for Carotid Atherosclerotic Plaques Based on in Vivo MRI Data", *Mol. Cell. Biomech.*, 6(2): 121-134 (2009).

Yang, C., et al., "In Vivo/Ex Vivo MRT-Based 3D Non-Newtonian FSI Models for Human Atherosclerotic Plaques Compared with Fluid/Wall-Only Models", *Comput. Model. Eng. Sci.*, 19(3): 233-245 (2007).

ADINA R&D, Inc. "Automatic Dynamic Incremental Nonlinear Analysis" ADINA System 8.2 Release Notes, Jan. 2005.

* cited by examiner (a) A human heart    (b) Segmented RV MRI contour plots    (c) RV FE Mesh (d) RV/LV from MRI    (e) Re-constructed RV/LV geometry (a) Sketch of RV with a Patch and Scar Tissue (b) RV Model with a Patch (c) RV with a Smaller Patch (a) Cut Surface-1, Left Part
(b) Right Portion
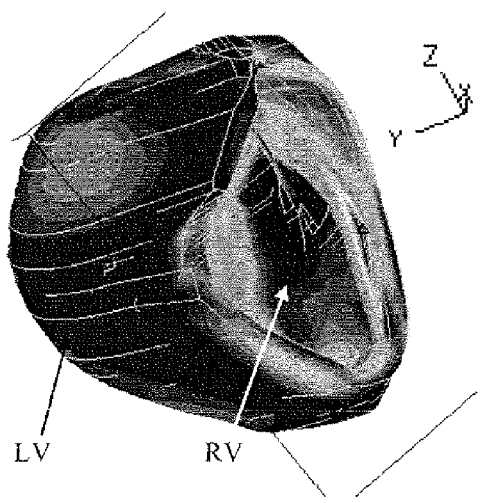
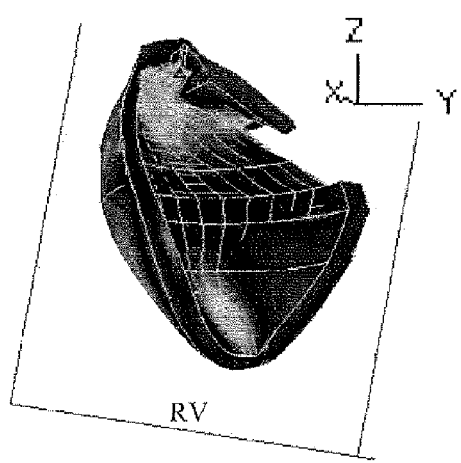
Min    Universal Scale    Max
FIGS. 6(a)-6(b)

(a) t=0.1s, beginning of filling
Unit: mmHg (b) t=0.35s, just before end of filling (c) t=0.37s, beginning of ejection
inlet closed, outlet just opened (d) t=0.39s, ejection continues.

(a) Stress-$P_1$ at maximum pressure, RV with patch, inner surface (b) Strain-$P_1$ at maximum pressure, RV with patch, inner surface (c) Stress-$P_1$, 3D view (d) Strain-$P_1$, 3D view (a) Tracking locations marked on Patched RV Strain-P1 plot (b) Stress-$P_1$, No Patch (c) Stress-$P_1$, with Patch (d) Strain-$P_1$, No Patch (e) Strain-$P_1$, with Patch (a) Segmented RV/LV Contours (b) RV-LV Geometries (c) Valve Locations (d) Locations of Patch and Scar Tissue (e) Inflated Whole Model, Strain-$P_1$ shown (a) New patch model contours overlapping pre-op model contours post-s2 vs. pre-s2   post-s3 vs. pre-s4   post-s4 vs. pre-s5   post-s5 vs. pre-s6   post-s6 vs. pre-s7 post-s7 vs. pre-s9   post-s8 vs. pre-s10   post-s9 vs. pre-s11   post-s10 vs. pre-s12   post-s11 vs. pre-s13

(b) A sample for overlapping contours from three (a) Post-Op CMR Images (10 selected from 12 slices) from the Same Patient.

(b) Computational Pre- and Post-Op Pressure Conditions in RV.

(c) Computer-Predicted and CMR-Measured RV Volumes.

(a) RV Volume from Passive Model Compared with CMR Data (b) RV Volume from Active Model Compared with CMR Data (a) Filling Phase  (b) Ejection Begins  (c) Ejection Continues
FIGS. 29(a)-29(f)
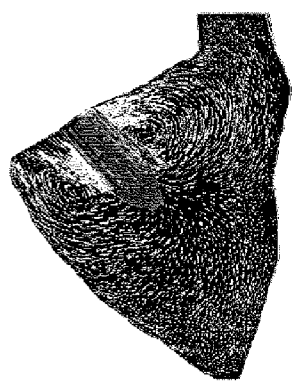
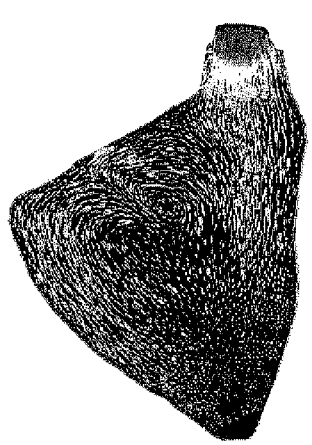
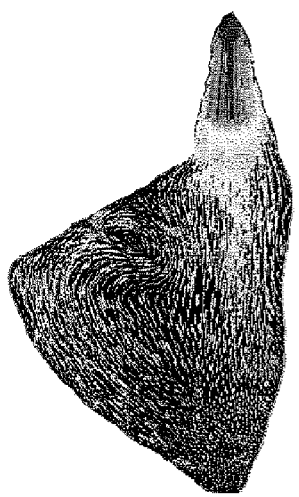
(d) Filling Phase  (e) Ejection Begins  (f) Ejection Continues
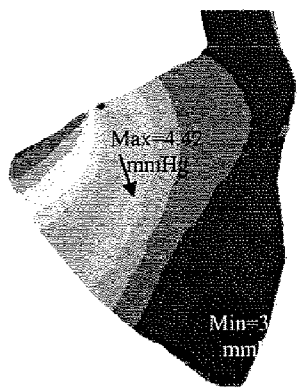
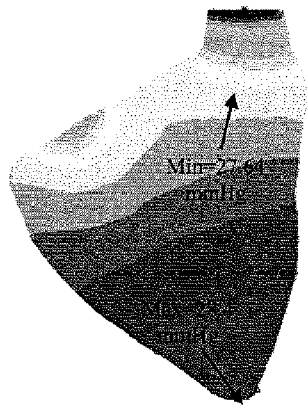
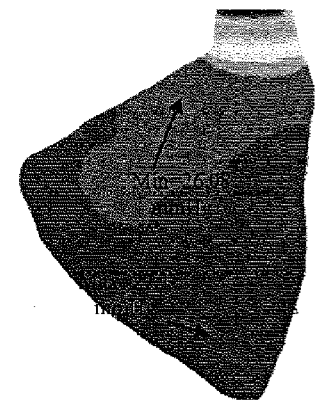
Max　　Universal Scale　　Min
FIGS. 29(a)-29(f)

(a) M1: Pre-Op Model.    (b) M2: Patch Model 1.    (c) M3: Patch Model 2.

(a) Post-Op CMR Images (10 selected from 12 slices) from the Same Patient.

(b) Computational Pre- and Post-Op Pressure Conditions in RV.

(c) Computer-Predicted and CMR-Measured RV Volumes.

PATIENT-SPECIFIC IMAGE-BASED COMPUTATIONAL MODELING AND TECHNIQUES FOR HUMAN HEART SURGERY OPTIMIZATION

RELATED APPLICATION

This application claims the benefit of U.S. Provisional Application No. 60/931,282, filed on May 22, 2007. The entire teachings of the above application are incorporated herein by reference.

BACKGROUND OF THE INVENTION

Heart disease is the number one killer in the United States. Heart attacks kill nearly a million Americans a year—rich and poor, the famous and the forgotten. In fact, cardiovascular disease is so common that 64 million Americans suffer from some form of it (and 39 million of these people are age 65 years old or younger). Right ventricular (RV) dysfunction is one of the more common causes of heart failure in patients with congenital heart defects and often leads to impaired functional capacity and premature death. Patients with repaired Tetralogy of Fallot (ToF), a congenital heart defect which includes a ventricular septal defect and severe RV outflow obstruction, account for the majority of cases with late onset RV failure. The mechanism of failure is a complex interaction of chronic pulmonary valve regurgitation (present since the original repair), a non-contractile and sometimes aneurysmal RV outflow, ventricular scarring from the incision to remove RV outflow muscle at the original repair, and some residual obstruction to RV outflow. It is believed that mechanical factors play an important role in the development of the disease leading to RV failure.

Image-based computational modeling and medical imaging technologies have made considerable advances in biological and clinical research in recent years (Axel, L., 2002, "Biomechanical Dynamics of the Heart With MRI," Annu. Rev. Biomed. Eng., 4, pp. 321-347; Bloomgarden, D. C., Fayad, Z. A., Ferrari, V. A., Chin, B., Sutton, M. G., and Axel, L., 1997, "Global Cardiac Function Using Fast Breath-Hold MRI: Validation of New Acquisition and Analysis Techniques," Magn. Reson. Med., 37, pp. 683-692; Geva, T., Greil, G. F., Marshall, A. C., Landzberg, M., and Powell, A. J., 2002, "Gadolinium-Enhanced 3-Dimensional Magnetic Resonance Angiography of Pulmonary Blood Supply in Patients With Complex Pulmonary Stenosis or Atresia: Comparison With X-Ray Angiography," Circulation, 106, pp. 473-478; Geva, T., Powell, A. J., Crawford, E. C., Chung, T., and Colan, S. D., 1998, "Evaluation of Regional Differences in Right Ventricular Systolic Function by Acoustic Quantification Echocardiography and Cine Magnetic Resonance Imaging," Circulation, 98, pp. 339-345; Geva, T., Sandweiss, B. M., Gauvreau, K., Lock, J. E., and Powell, A. J., 2004, "Factors Associated With Impaired Clinical Status in Long-Term Survivors of Tetralogy of Fallot Repair Evaluated by Magnetic Resonance Imaging," J. Am. Coll. Cardiol., 43, pp. 1068-1074; Guccione, J. M., K. D. Costa, A. D. McCulloch, (1995) J. Biomech. 28(10), 1167-77; Guccione, J. M., A. D. McCulloch, L. K. Waldman, (1991) J Biomech Eng. 113(1), 42-55; Guccione, J. M., G. S. Le Prell, P. P. de Tombe, W. C. Hunter, (1997) J. Biomech. 30(2), 189-192; Guccione, J. M., A. D. McCulloch, (1993) J Biomech Eng. 115(1), 72-81; Guccione, J. M., L. K. Waldman, A. D. McCulloch, (1993) J Biomech Eng. 115(1), 82-90; Holzapfel, G. A., T. C. Gasser, R. W. Ogden, (2000) Journal of Elasticity, 61, 1-48; Holzapfel G. A., M. Stadler, C. A. J. Schulze-Bause, (2002) Annals of Biomedical Engineering, 30(6), 753-767; J. D. Humphrey, Cardiovascular Solid Mechanics, Springer-Verlag, New York, 2002; P. J. Hunter, A. J. Pullan, B. H. Smaill, "Modeling total heart function," Annu Rev Biomed Eng., 5:147-177, 2003; Kuehne, T., Yilmaz, S., Steendijk, P., Moore, P., Groenink, M., Saaed, M., Weber, O., Higgins, C. B., Ewert, P., Fleck, E., Nagel, E., Schulze-Neick, I., and Lange, P., 2004, "Magnetic Resonance Imaging Analysis of Right Ventricular Pressure-Volume Loops In Vivo Validation and Clinical Application in Patients With Pulmonary Hypertension," Circulation, 110, pp. 2010-2016; McCulloch, A. M. et al., (2007) Continuity 6 (a package distributed free by the National Biomedical Computation Resource); McCulloch, A. M., L. Waldman, J. Rogers, J. Guccione, (1992) Critical Rev. in Biomedical Engineering, 20(5,6): 427-449; M. P. Nash, P. J. Hunter, "Computational Mechanics of the Heart, From Tissue Structure to Ventricular Function," Journal of Elasticity, 61:113-141, 2000; C. S. Peskin, Mathematical Aspects of Heart Physiology, Lecture Notes of Courant Institute of Mathematical Sciences, New York, 1975; Peskin, C. S., D. M. McQueen, (1992) Crit Rev Biomed Eng. 20(5-6), 451-459; J. M. Rogers and A. D. McCulloch, "Nonuniform muscle fiber orientation causes spiral wave drift in a finite element model of cardiac action potential propagation," J Cardiovasc Electrophysiol. 5(6): 496-509, 1994; N. R. Saber, A. D. Gosman, N. B. Wood, P. J. Kilner, C. L. Charrier, and D. N. Firman, "Computational flow modeling of the left ventricle based on in vivo MRI data: initial experience," Annals of Biomech. Engng., 29:275-283, 2001; M. S. Sacks and C. J. Chuong, "Biaxial mechanical properties of passive right ventricular free wall myocardium," J Biomech Eng, 115:202-205, 1993; C. Stevens and P. J. Hunter, "Sarcomere length changes in a 3D mathematical model of the pig ventricles," *Progress in Biophysics & Molecular Biology*, 82:229-241, 2003; C. Stevens, E. Remme, I. LeGrice, P. J. Hunter, "Ventricular mechanics in diastole: material parameter sensitivity," *J Biomech.*, 36(5): 737-48, 2003; D. Tang, C. Yang, J. Zheng, P. K. Woodard, G. A. Sicard, J. E. Saffitz, and C. Yuan, "3D MRI-Based Multi-Component FSI Models for Atherosclerotic Plaques a 3-D FSI model," *Annals of Biomedical Engineering*, 32(7):947-960, 2004; Tang D, Yang C, Zheng J, Woodard P K, Saffitz J E, Petruccelli J D, Sicard G A, Yuan C. "Local maximal stress hypothesis and computational plaque vulnerability index for atherosclerotic plaque assessment." Ann Biomed Eng 2005; 33(12):1789-1801; T. P. Usyk, A. D. McCulloch, "Relationship between regional shortening and asynchronous electrical activation in a three-dimensional model of ventricular electromechanics," J Cardiovasc Electrophysiol., 14(10 Suppl): S196-202, 2003; F. J. Vetter and A. D. McCulloch, "Three-dimensional stress and strain in passive rabbit left ventricle: a model study," *Annals of Biomech. Engng.* 28:781-792, 2000; Vliegen, H. W., Van Straten, A., De Roos, A., Roest, A. A., Schoof, P. H., Zwinderman, A. H., Ottenkamp, J., Van Der Wall, E. E., and Hazekamp, M. G., 2002, "Magnetic Resonance Imaging to Assess the Hemodynamic Effects of Pulmonary Valve Replacement in Adults Late After Repair of Tetralogy of Fallot," Circulation, 106, pp. 1703-1707). Use of computer-assisted procedures is becoming more and more popular in clinical decision making processes and computer-aided surgeries. Early three-dimensional (3D) models for blood flow in the heart include Peskin's model which introduced fiber-based left ventricle (LV) model and the celebrated immersed-boundary method to study blood flow features in an idealized geometry with fluid-structure interactions (FSIs; Peskin, 1975, see above). A large amount of effort has been devoted to quantifying heart tissue mechanical properties and fiber orientations mostly using animal models (K. D. Costa, Y.

Takayama, A. D. McCulloch, J. W. Covell, "Laminar fiber architecture and three-dimensional systolic mechanics in canine ventricular myocardium," Am J. Physiol. 276(2 Pt 2):H595-607, 1999; Nash and Hunter, 2000, see above; Rogers and McCulloh, 1994, see above; Sacks and Chuong, 1993, see above; Y. Takayama, K. D. Costa, J. W. Covell, "Contribution of laminar myofiber architecture to load-dependent changes in mechanics of LV myocardium," Am J Physiol Heart Circ Physiol. 282(4):H1510-20, 2002). Humphrey's book provides a comprehensive review of the literature (Humphrey, 2002, see above).

More recent efforts include introduction of magnetic resonance image (MRI)-based fluid-only or structure-only 3D models to investigate flow and stress/strain behaviors in the whole ventricle (either RV or LV) (Guccione, Costa and McCulloch, 1995, see above; Guccione, McCulloch and Waldman, 1991, see above; Guccione et al., 1997, see above; Guccione and McCulloch, 1993, see above; Guccione, Waldman and McCulloch, 1993, see above; K. May-Newman and A. D. McCulloch, "Homogenization modeling for the mechanics of perfused myocardium," Prog Biophys Mol Biol. 69(2-3):463-81, 1998; McCulloch et al., 2007, see above; McCulloch et al., 1992, see above; Nash and Hunter, 2000, see above; Saber et al., 2001, see above; Sacks and Chuong, 1993, see above; Stevens and Hunter, 2003, see above; Stevens et al., 2003, see above; Usyk and McCulloch, 2003, see above; Tang et al., 2004, see above; F. J. Vetter and A. D. McCulloch, "Three-dimensional analysis of regional cardiac function: a model of rabbit ventricular anatomy," Prog Biophys Mol Biol. 69(2-3):157-183, 1998; Vetter and McCulloch, 2000, see above).

Stevens et al. introduced a 3D finite element (FE) solid model of the heart based on measurements of the geometry and the fiber and sheet orientations of pig hearts. The end-diastolic deformation of the model was computed using the "pole-zero" constitutive law to model the mechanics of passive myocardial tissue specimens. The sensitivities of end-diastolic fiber-sheet material strains and heart shape to changes in the material parameters were investigated (Stevens and Hunter, 2003, see above; Stevens et al., 2003, see above).

McCulloch et al. performed extensive research for 3D ventricular geometry and myofiber architecture of the rabbit heart. Their work and their Continuity package included experimental and modeling studies of 3D cardiac mechanics and electrophysiology (May-Newmand and McCulloch, 1998, see above; McCulloch et al., 2007, see above; McCulloch, Waldman and Guccione, 1992, see above; Usyk and McCulloch, 2003, see above; T. P. Usyk and R. Kerckhoffs, "Three dimensional electromechanical model of porcine heart with penetrating wound injury," Stud Health Technol Inform., 111:568-573, 2005; Vetter and McCulloch, 1998, see above; Vetter and McCulloch, 2000, see above).

In a series of papers, Guccione et al. introduced anisotropic passive and active ventricle models where an additional tension term was added to the stress field to model active heart contractions RV (Guccione, Costa and McCulloch, 1995, see above; Guccione, McCulloch and Waldman, 1991, see above; Guccione et al., 1997, see above; Guccione and McCulloch, 1993, see above; Guccione, Waldman and McCulloch, 1993, see above).

The papers by Nash and Hunter (see above) and Hunter, Pullan and Smaill (see above) provided comprehensive reviews for heart modeling, including tissue properties, fiber orientation, passive and active mechanical models, electro-mechanical models, and whole heart models. Those animal models provide some insight for human heart mechanics and function with a huge effort and great detail.

SUMMARY OF THE INVENTION

The present invention discloses patient-specific image-based computational modeling and techniques for human heart surgery optimization.

In one embodiment of the present invention, a method for determining cardiac status comprises, for a given patient, constructing a patient-specific, three-dimensional, computational model of the patient's heart; and executing the constructed computational model, said executing generating a quantitative analysis of cardiac function. The step of constructing can comprise basing the model on patient-specific data including one or more of the data from ventricle morphology, cardiac motion, blood flow, material properties and pressure and volume conditions. The method can further comprise constructing a three-dimensional, computational model of a healthy heart to serve as baseline control. The model can include any one or combination of: right ventricle, left ventricle, and patch and scar tissues. The model can include any one or combination of: fluid-structure interactions, valve mechanics, pulmonary regurgitation, fiber orientation and single-, double-, or multiple-layer anisotropic models, and an active contraction model. The method can also comprise validating the model with patient-specific data.

In another embodiment of the present invention, a method of performing cardiac surgeries comprises: a) assessing surgical options based on a patient-specific, three-dimensional, computational model of a patient's heart; and b) performing surgery based on one or more of the surgical options. The model can be based on patient-specific data including one or more of the data from ventricle morphology, cardiac motion, blood flow, material properties and pressure and volume conditions. The model can include any one or combination of: right ventricle, left ventricle, and patch and scar tissues. The model can include any one or combination of: fluid-structure interactions, valve mechanics, pulmonary regurgitation, fiber orientation and single-, double-, or multiple-layer anisotropic models, and an active contraction model. The model can be validated with patient-specific data. The step of assessing can comprise computationally designing surgical options. The method can further comprise: c) constructing predictive models of post-operative outcome for one or more of the surgical options; d) providing post-surgery data; and e) validating or adjusting the predictive models based on the post-surgery data.

In still another embodiment of the present invention, a computer system comprises: a) a data source containing data of a patient's heart; b) a modeler coupled to receive data from the data source, the modeler generating a patient-specific, three-dimensional, computational model of the heart based on the heart data; and c) a processor routine for computationally providing information about a certain cardiac function using the three-dimensional heart model and for applying computational, quantitative analysis of the cardiac function, wherein the quantitative analysis of the cardiac function provides an assessment for surgical options, optimizing surgical techniques, or predicting outcomes. The heart data can include one or more patient-specific data comprising: ventricle morphology, cardiac motion, blood flow, material properties and pressure and volume conditions. The model can include any one or combination of: right ventricle, left ventricle, and patch and scar tissues. The model can include any one or combination of: fluid-structure interactions, valve mechanics, pulmonary regurgitation, fiber orientation and single-, double-, or multiple-layer anisotropic models, and an active contraction model.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 6(a)-6(b) are schematic illustrations showing position of the cut-surface selected for presentation of 3D results.

FIGS. 19(a)-19(c) show Strain-$P_1$ distributions from the three models are used to show locations of tracking sites. Selected tracking points and marking symbols in the plots: X1: *, just below the patch (or scar for M2); X2: x, just next to the left of the patch; X3: o, just above the patch; X4: +, just next to the right of the patch; X5: v, at the center of the patch; X6: ˆ, just below the patch (this is for pre-op model only).

FIGS. 29(a)-29(f) are flow velocity and pressure band plots during the filling and ejection phases showing interesting patterns.

DETAILED DESCRIPTION OF THE INVENTION

Figure 1:
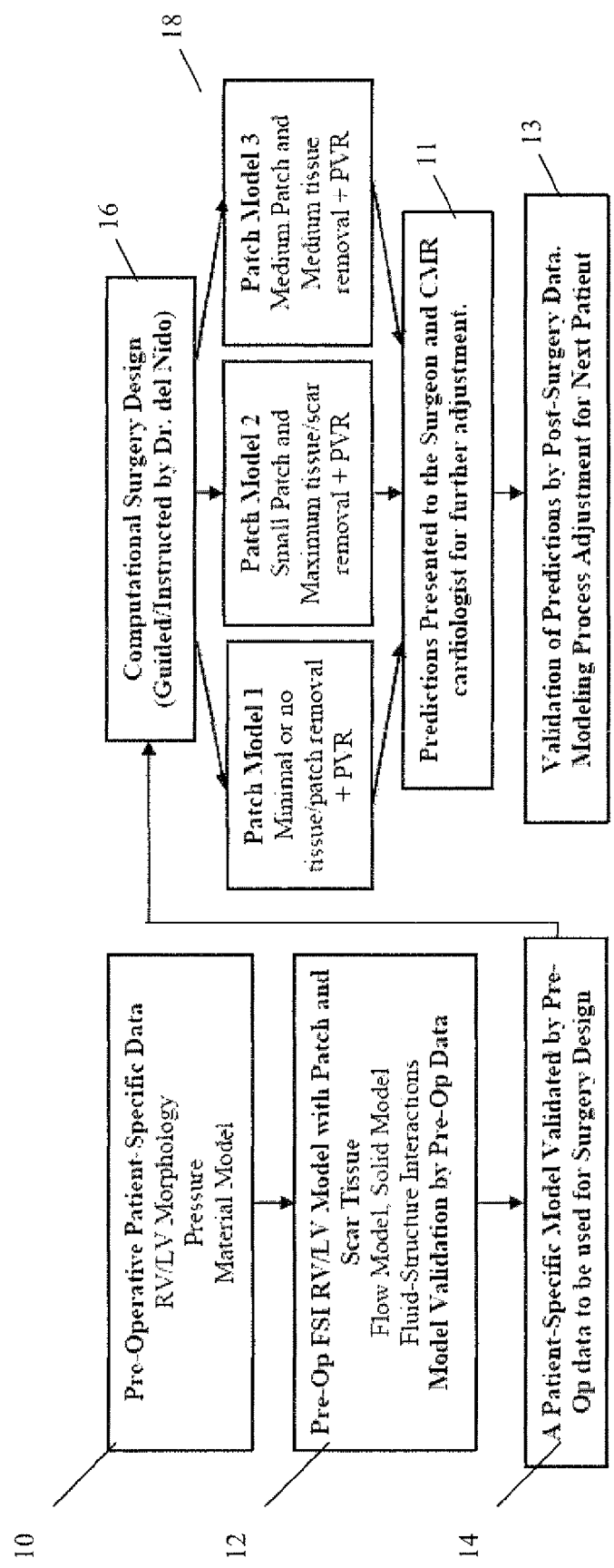
FIG. 1 is a flowchart showing model development and a validation process of the present invention.
Figure 2A:
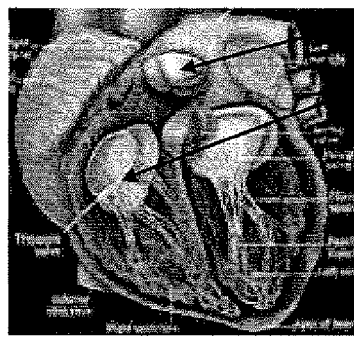
FIGS. 2(a)-2(e) are basic plots showing the modeling procedure of the present invention: (a) A healthy human heart sketch showing left and right ventricles with valve positions; (b) segmented RV MRI contour plots; (c) 3D FE mesh for the RV showing valve positions; (d) RV/LV geometry from MRI; (e) the re-constructed 3D geometry of the RV/LV combination model.
Figure 2B:
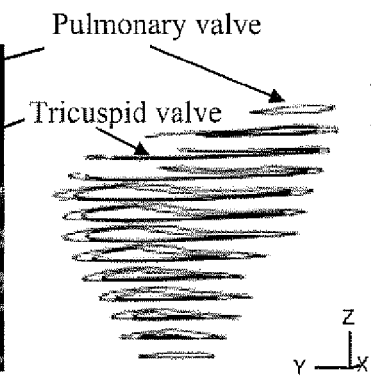
Figure 2C:
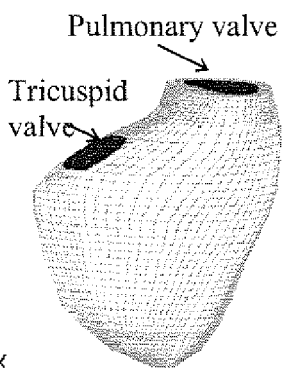
Figure 2D:
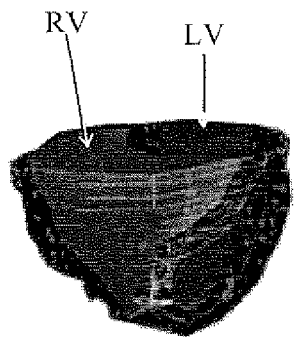
Figure 2E:
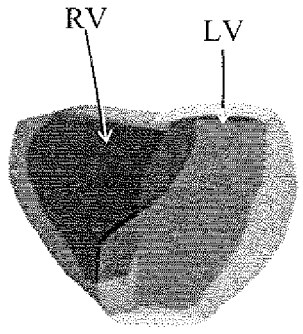

A description of example embodiments of the invention follows.

The teachings of all patents, published applications and references cited herein are incorporated by reference in their entirety.

Due to the complexity of human heart structure, nonlinear anisotropic tissue material properties, and difficulties involved in acquiring human subject data and solving models including fluid-structure interactions (FSIs), patient-specific right ventricle (RV) models with FSI for actual surgery planning and optimization based on and verifiable by clinically-available data are lacking in the current literature and clinical practice. So far, no models involve patient-specific data including ventricle morphology, material properties, pressure conditions, patch and scar tissues. No models involve model validation by patient-specific pre- and post-operation data. No models include fluid-structure interactions the way the current invention has.

Applicant discloses a novel integrated modeling process which models human ventricle blood flow and heart motions, assesses ventricle cardiac functions, and optimizes surgical techniques for RV anterior wall volume reduction and remodeling related to pulmonary valve replacement/insertion. A heart of the present invention is based on patient-specific data including ventricle morphology, material properties, and pressure conditions. The model includes RV, left ventricle (LV), patch, and scar tissues. FSI and RV/LV/Patch/Scar interactions are also included in the model. According to the present invention, mechanical analysis can include both flow and solid stress/strain results. The patient-specific model can be validated by pre- and post operation data from the same patient and has potential for optimized surgery recommendations. The present invention is also directed to specific procedures to evaluate ventricle cardiac functions and assess surgical outcome improvement. According to the present invention, localized flow and stress/strain information can be used to assess surgical options. The present invention can have direct clinical and surgical applications.

The complexity of the problem makes it necessary to make some model simplifications so that the model can be based on clinically-measurable data, simple enough to be solved for a quick turn-around time (ideally within 24-48 hours when implemented for clinical use), and yet capture key factors to assess RV cardiac function (RV stroke volume (SV) and ejection fraction (EF)) and make accurate and verifiable predictions needed in the surgery design. In a preferred embodiment, the model is based on patient-specific ventricle morphology, flow and pressure data. Fiber orientations and active contracting forces are included in the current model when such data are available in clinical practice and the time and effort needed for model construction and solution makes it practical to use them in real surgery design. Fiber orientation in diseased ventricle with a patch and scar tissues is far more complex than that in a healthy chamber of the heart. Contracting forces are closely tied to fiber orientation. Including "theoretically assumed" fiber orientations and contracting forces may not improve the predictive power of the model since embodiments of the invention use RV volume and EF as the endpoint index, and models with or without the added features will likely achieve similar accuracy level as with the model of the present invention, (the error margin of the present invention is <3% for RV volume prediction) by adjusting model parameters.

The surgical, non-invasive cardiac magnetic resonance (CMR) imaging and computational modeling aspects of the present invention are integrated to optimized patch design and RV volume reduction surgery procedures to maximize recovery of RV function. FIG. 1 shows applicant's modeling development and validation plan. Three-dimensional (3D) magnetic resonance imaging (MRI)-based RV/LV/Patch combination models (see below) with FSI are employed in the present invention. The design procedures require four steps: (a) Upon receiving pre-operative data 10, a pre-operation model 14 is constructed. Patient-specific material parameters are determined using measured RV pressure and volume data so that computational and CMR volume data reach good agreement 12. (b) Using the patient-specific model 14 validated (at 12) by pre-operative data and surgeon guidance (step 16), different patch models as indicated at 18 in the flowchart are constructed to make predictions for post-operative outcome. (c) After the surgery, computational mechanical analysis and predicted RV cardiac function improvements are provided (step 11) to surgeons/health care professionals for their review after the operation. (d) Post-operative data are obtained from the same patient six months after the operation to serve as short-term validation 13 of the proposed surgical procedures. The predictive model 14 is adjustable (morphology, material properties, patch and scar information, pressure conditions) to improve the accuracy of computational predictions. The models, surgical and patch design procedures are continuously improved 13 as more experience is gained.

Example 1

Data Acquisition using CMR

CMR is ideally suited for noninvasive evaluation of cardiovascular anatomy and function. Quantitative CMR techniques can accurately measure biventricular systolic function irrespective of chamber geometry and quantify blood flow in any desired location, including quantification of pulmonary regurgitation (PR). CMR has been used extensively by the applicant and by other investigators in patients with Tetralogy of Fallot (ToF) and its accuracy and reproducibility in assessing RV dimensions, function and quantification of PR have been validated. The applicant routinely performs CMR in patients with repaired ToF once they reach an age when they can cooperate with the examination (usually by age 10-11 years). Preliminary patient-specific ventricle morphologies, cardiac motions and flow data are acquired using standardized clinical protocols. CMR data can be obtained pre- and post-operation. CMR is used to acquire patient-specific ventricle geometry, heart motion, flow velocity, and flow rate for patients needing RV remodeling and pulmonary valve replacement operations before and after scheduled surgeries and for healthy volunteers to serve as baseline controls. Accurate RV pressure measurements are obtained in the catheterization laboratory (performed routinely in theses patients prior to surgery and in follow-up) or in the operating room using direct pressure measurement in the RV. Data acquired are processed so that they can be used in computational work as further made clear below.

Example 2

Preliminary Results from 3D MRI-Based Computational Models

The motion of the human heart and related blood flow and structure stress/strain behaviors are very complex. The purpose of the computational modeling and simulation according to the present invention is to choose the proper models which include important factors concerning RV function and that can be solved within a reasonable time (e.g., 24 hours) so that surgeons can use the computational analysis to aid and optimize RV remodeling surgery. A 3D MRI-based RV-LV combination model with FSI was selected because a) it is based on clinically available patient-specific data (morphology, pressure, and flow); b) the FSI model makes it possible to combine fluid and structure models to analyze RV function with different patch designs and represents a starting point for many further improvements; c) it can provide accurate and reliable assessment of RV function prior to surgery. Its predictions for RV function, such as SV and EF are verified and validated by patient data, pre- and post-operatively as part of the present invention. SV and EF are well accepted indices for RV function assessment and serve as end-points for the optimization procedures. Based on pt. exclusion criteria of significant pre-operative RV outflow obstruction, RV after load should not change significantly pre to post-surgery in the individual patient.

RV/LV morphology of a healthy human volunteer was acquired by using planar tagged MRI. Segmentation and 3D motion reconstruction were performed following known procedures (Haber I. Three-dimensional motion reconstruction and analysis of the right ventricle from planar tagger MRI. University of Pennsylvania, Ph.D. Dissertation; 2000). Ten positions of the RV/LV were acquired during one cardiac cycle, with each position containing 10-14 planar slices. 3D geometry of the RV/LV combination and computational mesh were constructed following known procedures (Tang et al., 2004, see above; Tang D, Yang C, del Nido P J, Haber I, Geva T, 3D Image-Based Computational Modeling for Patient-Specific Mechanical Analysis of Human Heart Right Ventricles, Proceedings of the 2005 International Conference on Mathematics and Engineering Techniques in Medicine and Biological Sciences (METMBS '05), 2005:190-196; Tang D, Yang C, Haber I, Geva T, del Nido P J, Image-Based RV/LV Combination Structure-Only and FSI Models for Mechanical Analysis of Human Right Ventricle Remodeling Surgery Design, J. Biomechanics, 2006; 9:S438.). FIGS. 2(a)-2(e) are illustrative of each of these phases. In particular, FIGS. 2(a)-2(e) show a figure of a human heart, segmented MRI contour plot of an RV, RV valve positions and 3D FE mesh, RV/LV geometry from MRI, and the reconstructed 3D geometry of the RV/LV combination model, respectively.

The RV, LV, scar tissue, and patch material are assumed to be hyperelastic, isotropic, nearly incompressible and homogeneous. The governing equations for the structure models are (summation convention is used; Fung, Y. C., 1994, A First Course in Continuum Mechanics: For Physical and Biological Engineers and Scientists, 3rd ed., Prentice-Hall, Englewood Cliffs, N.J.):

$$\rho v_{i,tt} = \sigma_{ij,j}, \text{ (equation of motion for solids)} \quad (1)$$

with i,j=1, 2, 3; sum over j, $$\epsilon_{ij} = (v_{i,j} + v_{j,i} + v_{\alpha,i} v_{\alpha,j})/2, \text{ (strain-displacement relation)} \quad (2)$$

with i,j, α=1, 2, 3; sum over α,
where α is the stress tensor (subscripts indicate different materials), ε is the Green's strain tensor, v is solid displacement vector, subscript tt in $v_{i,tt}$ indicates the second-order time derivative, $f_{,j}$ stands for derivative of the function f with respect to the jth variable, and ρ is material density. Equations (1)-(2) are used for RV/LV muscle, patch, and scar tissues, with parameter values adjusted for each material.

The nonlinear Mooney-Rivlin model was used to describe the nonlinear anisotropic and isotropic material properties of the material with parameter values chosen to match experimental data available and adjusted to reflect stiffness variation of different materials (Humphrey, 2002, see above; McColluch et al., 2007, see above; Sacks and Chuong, 2003, see above). The strain energy function for the isotropic modified Mooney-Rivlin model is given by (Bathe K. J, *Finite Element Procedures*. Prentice Hall, 1996; Bathe, 2002, Theory and Modeling Guide, ADINA R&D, Inc., Watertown, Mass., Vols. I and II; Yang, C., Tang, D., Haber, I., Geva, T., and del Nido, P. J., 2007, "In Vivo MRI-Based 3D FSI RV/LV Models for Human Right Ventricle and Patch Design for Potential Computer-Aided Surgery Optimization," Comput. Struct., 85, pp. 988-997):

$$W = c_1(I_1 - 3) + c_2(I_2 - 3) + D_1[\exp(D_2(I_1 - 3)) - 1], \quad (3)$$

$$I_1 = \Sigma C_{ii}, I_2 = \tfrac{1}{2}[I_1^2 - C_{ij} C_{ij}], \quad (4)$$

where $I_1$ and $I_2$ are the first and second strain invariants, $C = [C_{ij}] = X^T X$ is the right Cauchy-Green deformation tensor, $X = [X_{ij}] = [\partial x_i / \partial a_j]$, $(x_i)$ is current position, $(a_i)$ is original position, $c_i$ and $D_i$ are material parameters chosen to match experimental measurements (Humphrey, 2002, see above; McColluch et al., 2007, see above; Sacks and Chuong, 2003, see above). The 3D stress/strain relations can be obtained by finding various partial derivatives of the strain energy function with respect to proper variables (strain/stretch components). In particular, setting material density $\rho = 1$ g·cm$^{-3}$ and assuming, $$\lambda_1 \lambda_2 \lambda_3 = 1, \lambda_2 = \lambda_3, \lambda = \lambda_1, \quad (5)$$

where $\lambda_1$, $\lambda_2$ and $\lambda_3$ are stretch ratios in the (x,y,z) directions respectively, the uni-axial stress/stretch relation for an isotropic material is obtained from Equation (3), $$\sigma = \partial W / \partial \lambda = c_1 [2\lambda - 2\lambda^{-2}] + c_2 [2 - 2\lambda^{-3}] + D_1 D_2 [2\lambda - 2\lambda^{-2}] \exp[D_2 (\lambda^2 + 2\lambda^{-1} - 3)]. \quad (6)$$

Figure 3:
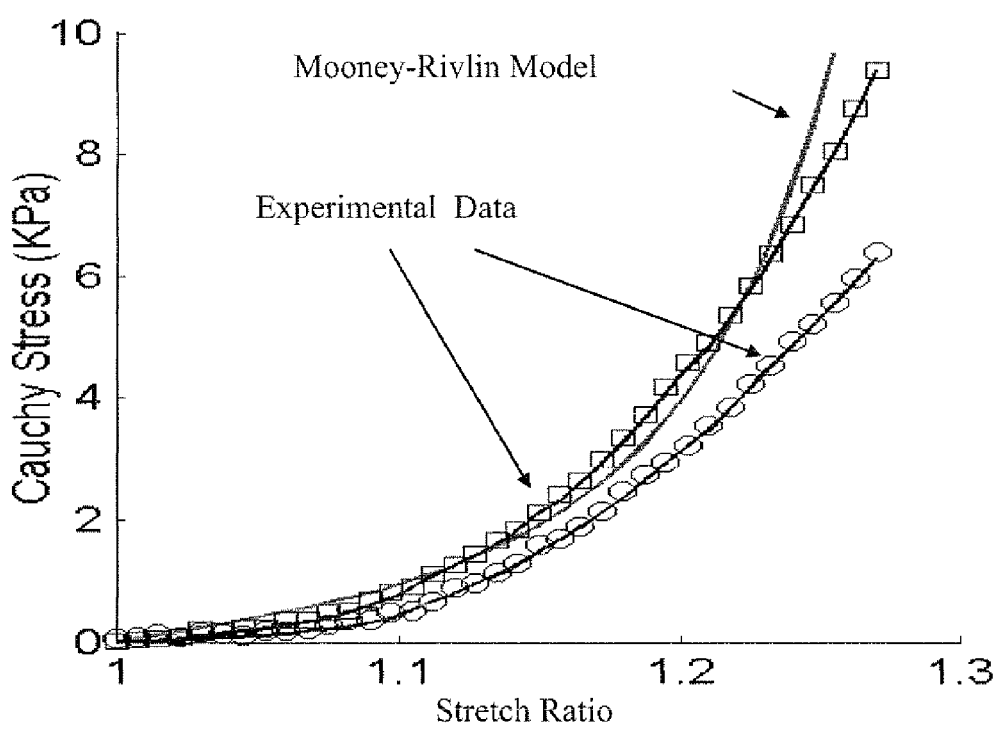
FIG. 3 is a graph showing experimental data for RV material properties and the stress-stretch curve derived from the Mooney-Rivlin model with parameters selected to fit experimental data. Parameter values used for the Mooney-Rivlin model include: $c_1=3600$ dyn/cm$^2$, $D_1=818$ dyn/cm$^2$, $c_2=0$, $D_2=12$.

The parameter values and stress-stretch curves fitting the experimental data are given by FIG. 3.

For problems with moving meshes, the physical observation that conservation of flux is needed is important; and indeed for mass and momentum on the mesh as the mesh changes or the nodes change positions. This requirement is well fulfilled using the FCBI elements and the FSI formulation in ADINA (ADINA R & D, Watertown, Mass.), a commercial FE package which is especially suitable for problems with fluid-structure interactions and large strain and deformations.

Figure 4A:
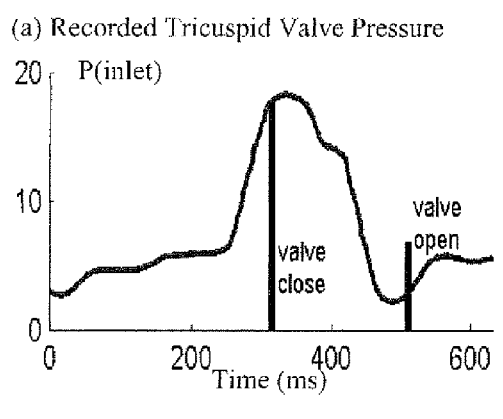
FIGS. 4(a)-4(b) are data graphs showing recorded pressure conditions at the tricuspid (inlet) and pulmonary (outlet) valves.
Figure 4B:
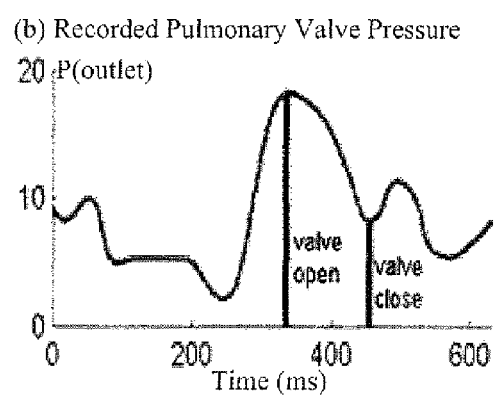
Figure 4C:
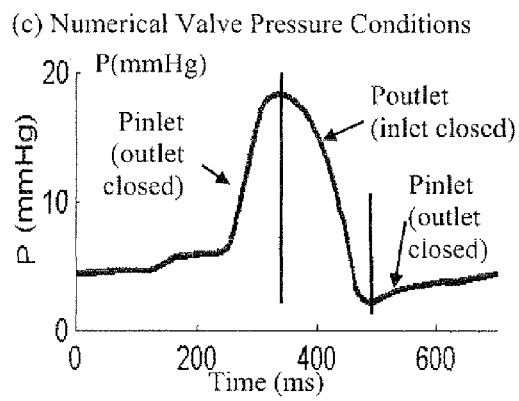
FIGS. 4(c)-4(d) are graphs showing prescribed numerical valve pressure conditions and valve close/open times. They were modified from the recorded data in FIGS. 4(a)-4(b) so that pressure conditions were as consistent with the recorded data as possible. The vertical bars indicate valve open/close switch time.
Figure 4D:
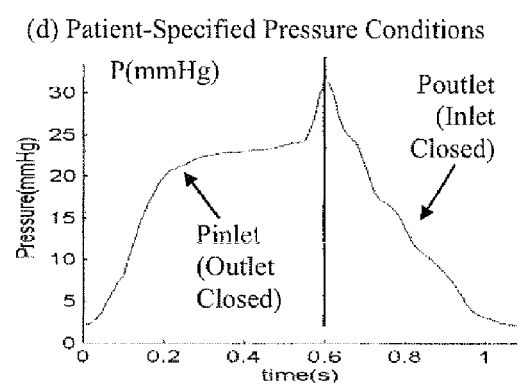

Blood flow in the right ventricle was assumed to be laminar, Newtonian, viscous and incompressible. The Navier-Stokes equations with ALE formulation are used as the governing equations. Computational pressure conditions are prescribed at the tricuspid (inlet) and pulmonary (outlet) valves matching recorded experimental data. The recorded and imposed numerical pressure conditions are given in FIG. 4(a)-4(c). FIG. 4(c) is a graph showing prescribed numerical valve pressure conditions. Valve close/open times were modified from the recorded data so that pressure conditions were as consistent with the recorded data in FIGS. 4(a)-4(b) as possible. The vertical bars in FIG. 4(c) indicate valve open/close switch times.

For this passive FSI model for normal RV, the simulation cycle was started when RV had its smallest volume (end of systole) corresponding to the minimal inlet pressure (t=480 ms, FIG. 4(c)). As the inlet pressure increases (inlet is kept open), blood flows into RV and its volume increases. When RV reaches its maximal volume, the tricuspid valve closes and the pulmonary valves opens up. Blood is ejected and RV volume decreases. That completes the cycle. While the mechanism driving the motion is different from the real actively contracting heart, the simulated RV motion, deformation, volume change, ejection fraction and fluid flow can provide results matching patient-specific data with properly-adjusted material parameters and flow-pressure boundary conditions. Simulations were conducted under various pressure and material conditions, with variations in patch geometry and stiffness to investigate their effect on RV functions. To simplify the computational model, the cardiac cycle was split into two phases: a) The filling phase when blood flows into RV, the inlet was kept open and the outlet was closed; b) The ejection phase when blood was ejected out of RV, the outlet was kept open and the inlet was closed. When the inlet or outlet were closed, flow velocity was set to zero at the valves and pressure was left unspecified (only one of the two conditions could be specified, or the system became over-determined). For ToF patients who's RV does not have a pulmonary valve, the outlet will be kept open with measured pressure condition specified to match measured outflow flow rate data.

When the inlet or outlet was closed, flow velocity was set zero at the valve and pressure was left unspecified:

$$P|_{inlet} = P_{inlet}(t), \text{ when inlet open;}$$

$$v|_{inlet} = 0, \text{ when inlet is closed;} \quad (7)$$

$$P|_{outlet} = P_{outlet}(t), \text{ when outlet open;}$$

$$v|_{outlet} = 0, \text{ when outlet is closed.} \quad (8)$$

For simplicity, LV is included as a structure-only model with the same material parameter values used for both LV and RV tissues. The inclusion of LV is important to obtain the correct RV motion and deformation and provides structure support for the part of RV surface connected to LV. Blood flow in LV can be included in the model given sufficient size of the computational code and total central processing unit (CPU) time. A uniform pressure was specified inside LV to keep its shape. A recorded LV pressure was specified inside the LV so that the LV will expand, contract and deform properly (Berne, R. M., M. N. Levy, B. M. Koeppen, B. A. Stanton, (2004) Physiology, Fifth Edition, Mosby, Elsevier, St. Louis, Mo.). No-slip boundary conditions and natural force boundary conditions were specified at all interfaces to couple fluid, RV, LV, and the patch models together.

Figure 5A:
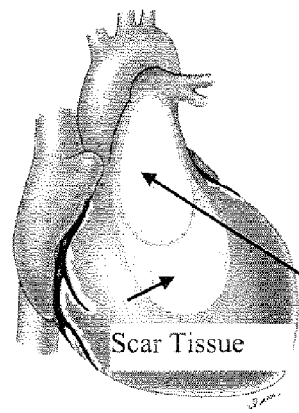
FIGS. 5(a)-5(c) are schematic illustrations showing RV patch shape and locations: (a) A diseased RV with a patch and scar tissues; (b) RV with a large patch; (c) RV with a small patch.
Figure 5B:
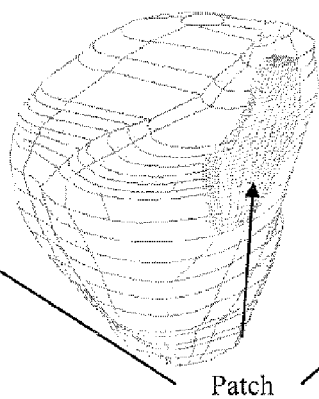
Figure 5C:
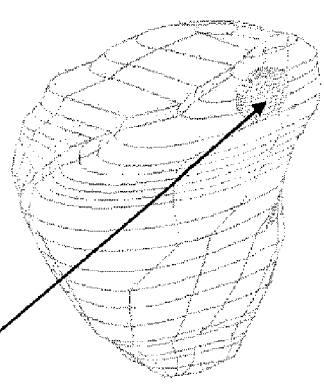

FIG. 5(a) shows a diseased RV with a patch and scar tissues. FIGS. 5(b)-5(c) show two patch models associated with pulmonary valve replacement surgery. The location, size and shape of a patch (or scar tissue) left on the right ventricle after resection were designed based on the protocol for the clinical trial (see T. Geva NIH/NHLBI 5P50HL074734 grant project) and the experience and guidance of a cardiac surgeon. The modified Mooney-Rivlin model was also used for the patch and scar tissue materials with parameters adjusted to reflect the stiffness variations.

CMR data was first acquired and segmented to get RV/LV geometries. Valve and patch positions were determined with flow data, delayed enhancement CMR to delineate location and extent of scar/patch, and the intra-operative observations of the surgeon. The computational mesh and finite element model were generated based on RV/LV geometries, valve locations and patch design. The complete LV/RV/Patch FSI model, which includes the fluid model, RV, LV, and patch models and all the associated boundary conditions and material constitutive laws, was solved by ADINA using unstructured finite elements and the Newton-Raphson iteration method. Nonlinear incremental iterative procedures were used to handle FSIs. Further details of FSI models and solution methods are given in Tang et al., 2004 (see above); Bathe, 1996, see above; and Bathe K J, Hou Z., "Finite element developments for general fluid flows with structural interactions." Int J Numer Method Eng 2004; 60: 213-32.

Figures 7A, 7B, 7C, 7D:
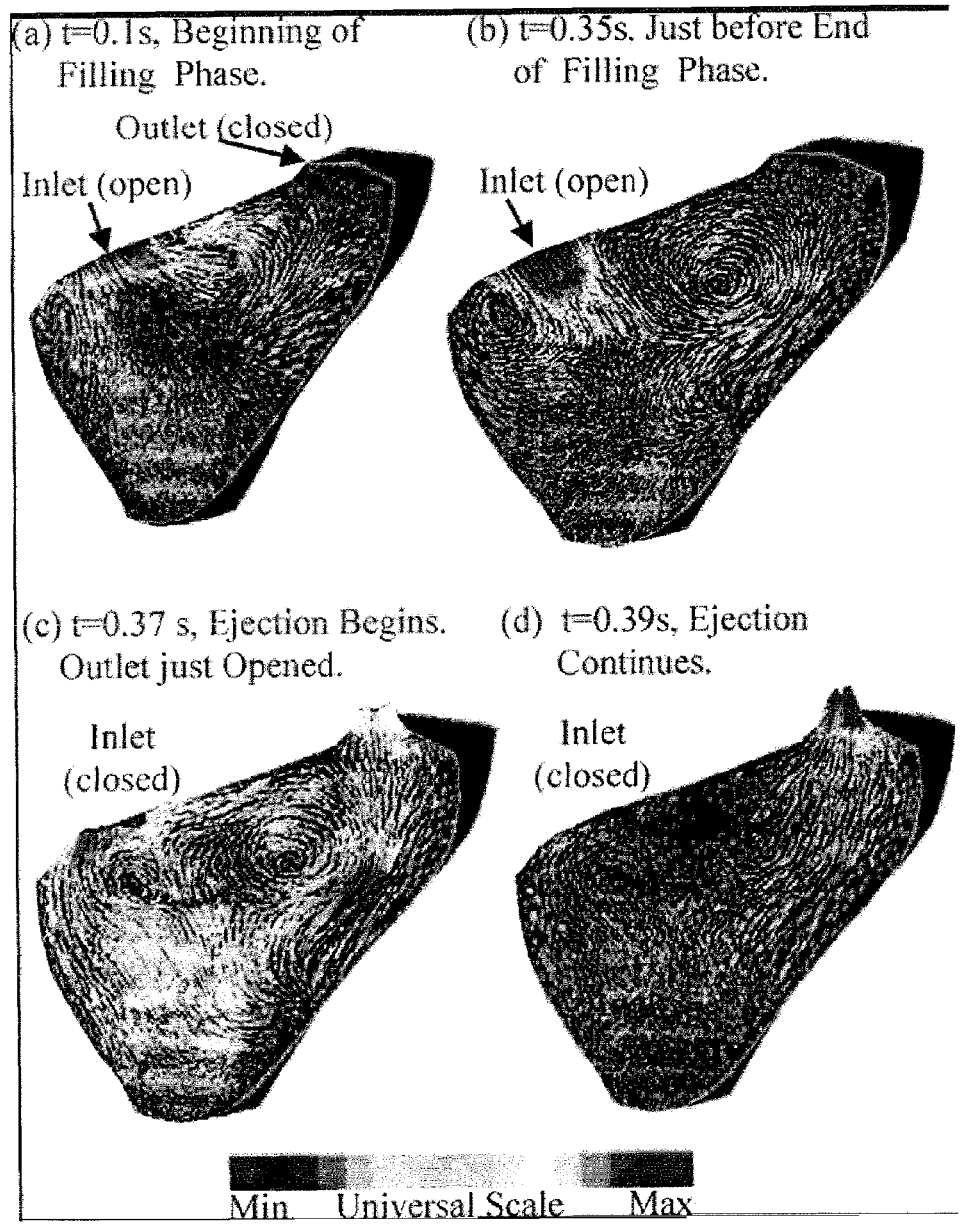
FIGS. 7(a)-7(d) are velocity plots at different phases showing interesting flow patterns: a) Beginning of the filling phase; b) flow patterns just before the end of filling phase; c) beginning of the ejection. The inlet just closed and the outlet valve is open. d) Ejection continues.

Preliminary results from the baseline RV/LV FSI model based on morphology obtained from a healthy volunteer are given below to demonstrate the basic features of the solutions. While the entire 3D solution data (which includes time-dependent 3D fluid velocity, pressure, RV stress/strain tensor distributions) need to be carefully searched to seek and identify critical information which may be useful in surgical planning and surgery optimization, some cut-surface should be selected for presentation purpose. FIG. 6(a)-6(b) show the position of a cut-surface chosen to present the results. FIGS. 7(a)-7(d) give some interesting flow patterns in the filling-ejection cycle. At t=0.1 s, the pressure gradient is small, filling is slow, as shown in FIG. 7(a). As the pressure gradient increases, flow velocity at the inlet increases which drives the flow in the RV and two vortices are observed (t=0.35 s) in FIG. 7(b). When the inlet closes and outlet just opens (t=0.37 s), another vortex forms near the inlet and flow starts to eject at the outlet, as shown in FIG. 7(c). At t=0.39 s, ejection becomes stronger, as shown in FIG. 7(d).

Figure 8A:
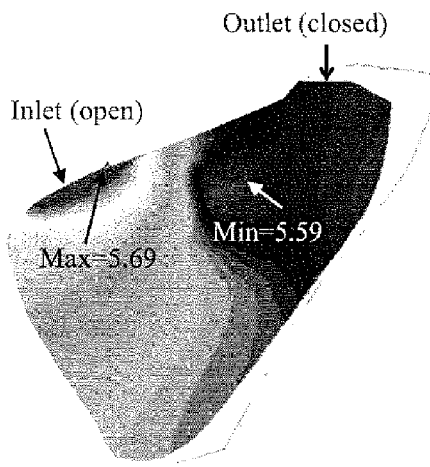
FIGS. 8(a)-8(d) are contour plots of pressure distributions on an x-cut surface at t=0.1 s, 0.35 s, 0.37 s and 0.39 s, respectively, corresponding to different RV filling and ejection phases as shown in FIGS. 7(a)-7(d). Unit for pressure: mmHg.
Figure 8B:
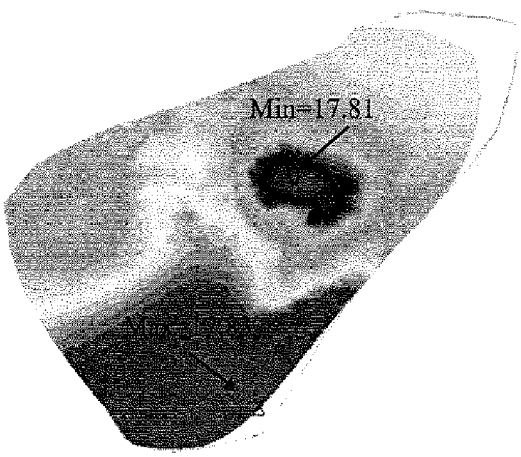
Figure 8C:
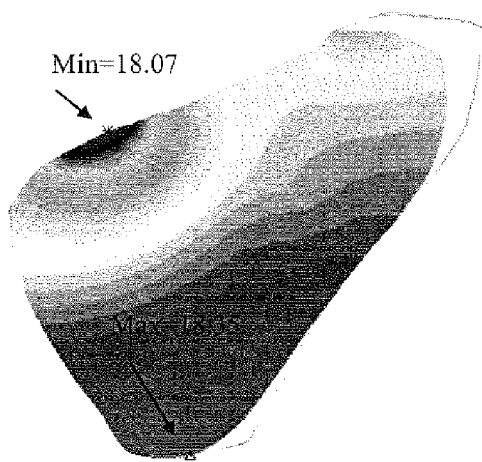
Figure 8D:
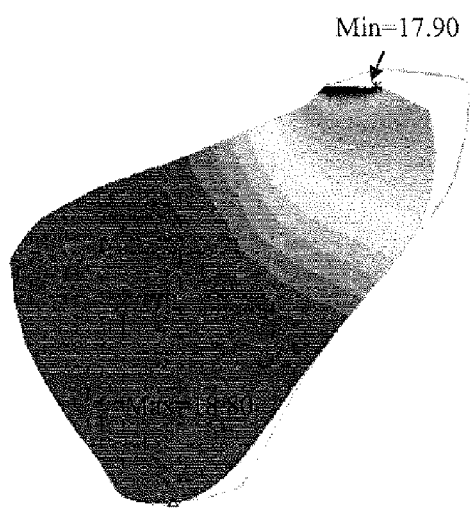

FIGS. 8(a)-8(d) give 4 pressure contour plots on the cut-surface corresponding to the velocity plots given by FIGS. 7(a)-7(d). At t=0.1 s, maximum pressure is found at the inlet, as indicated in FIG. 8(a). Minimum pressure was found at the inlet when it closes and ejection starts (see FIG. 8(c)). At t=0.39 s, minimum pressure was found at the outlet as ejection continued (FIG. 8(d)).

Figures 9A, 9B, 9C, 9D, 9E, 9F:
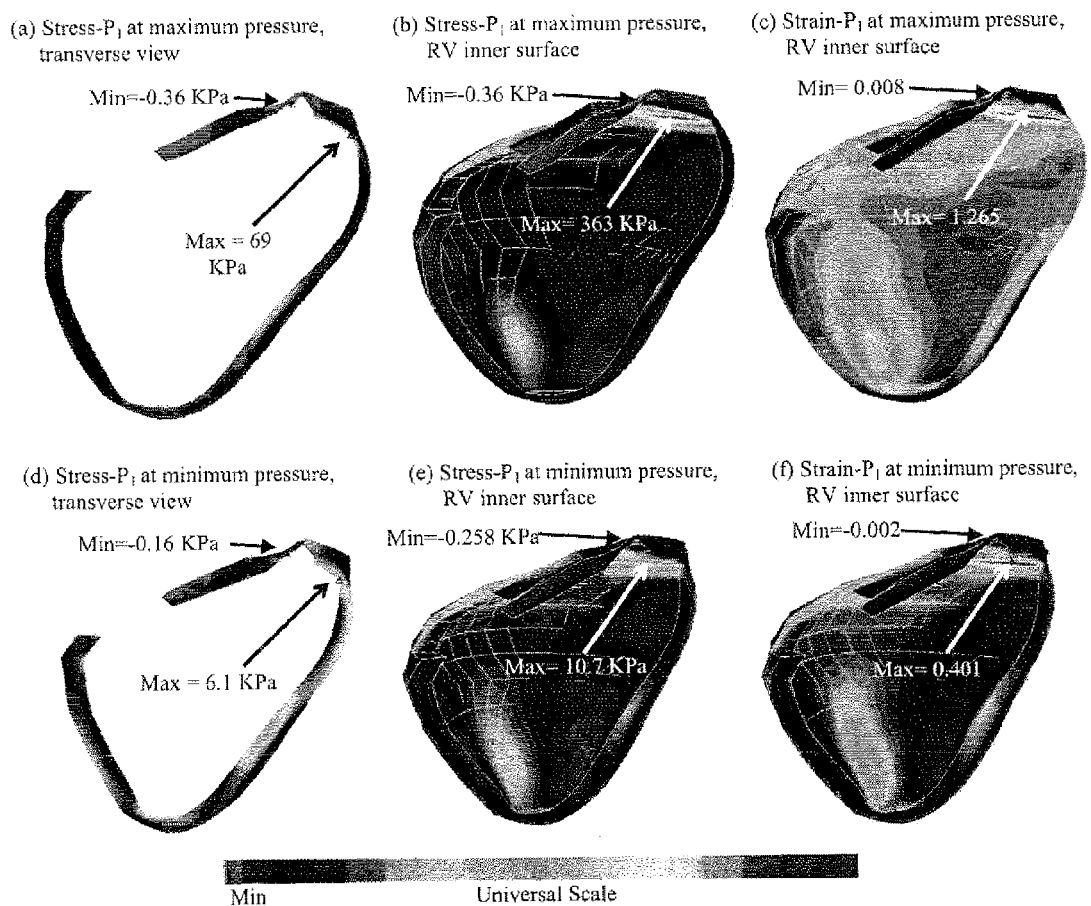
FIGS. 9(a)-9(f) are schematic views showing stress/strain distributions in the RV, which may provide useful information for mechanical analysis and disease state assessment: (a) transverse view of Stress-$P_1$ under maximum pressure; (b) Stress-$P_1$ on the inner surface of RV under maximum pressure; (c) Strain-$P_1$ on the inner surface of RV under maximum pressure; (d-f) stress/strain plots corresponding to minimum pressure condition.
Figure 10A:
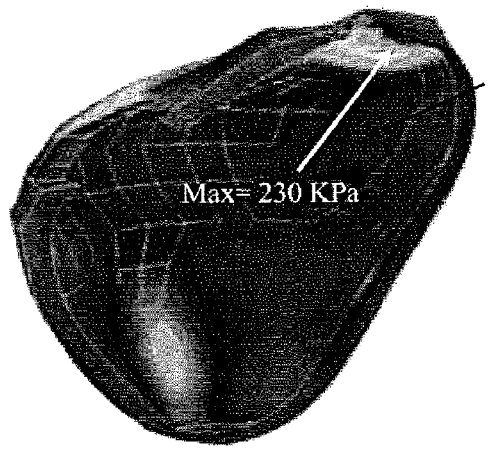
FIGS. 10(a)-10(d) are schematic views showing stress-$P_1$ and Strain-$P_1$ distributions in the RV with a patch.
Figure 10B:
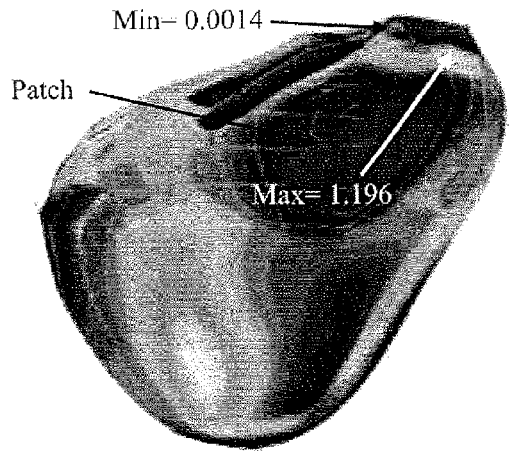
Figure 10C:
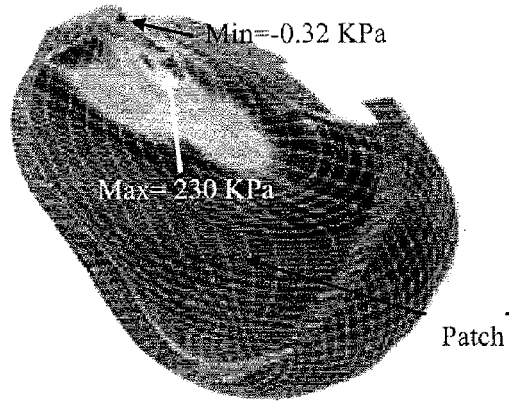
Figure 10D:
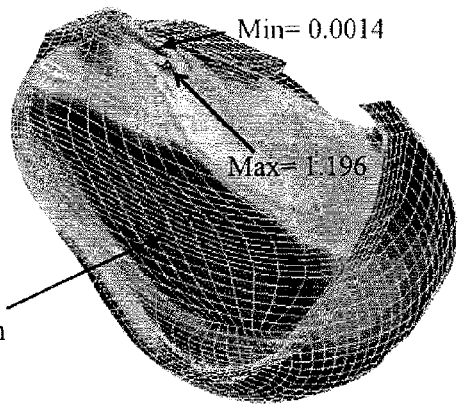
Figure 11A:
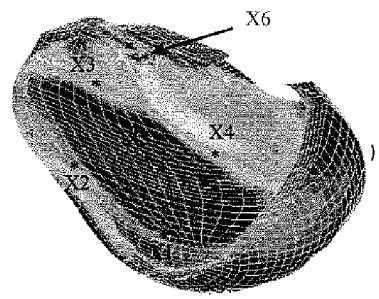
FIGS. 11(a)-11(e) are schematic and graph illustrations showing Stress-$P_1$ and Strain-$P_1$ tracked at 6 selected sites from the no-patch model and the patch model over a cardiac cycle providing local stress/strain behaviors. Differences of stress/strain variations at different locations can be as much as 1000% (10 times) in one cardiac cycle giving rich information for RV and patch analysis and assessment.
Figure 11B:
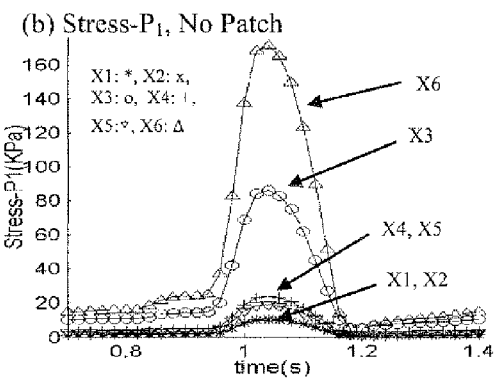
Figure 11C:
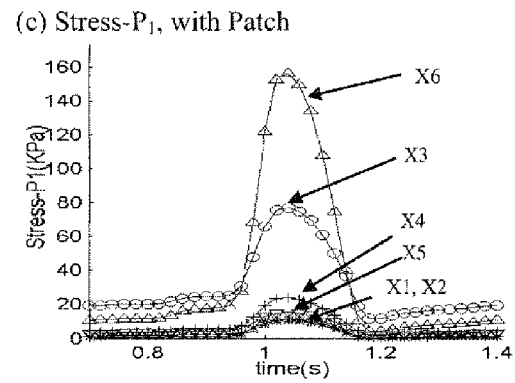
Figure 11D:
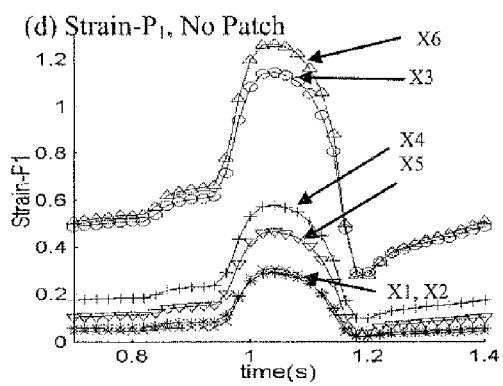
Figure 11E:
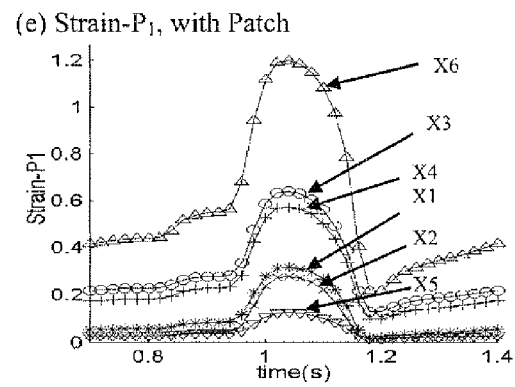

Maximal principal stress/strain (Stress-$P_1$ and Strain-$P_1$) distributions on the inner surface of the cut portion corresponding to both maximum and minimum imposed pressure conditions are given by FIGS. 9(a)-9(f). The figures were flipped horizontally to have the same position as that in FIGS. 7(a)-7(d) and 8(a)-8(d). Maximum stress and strain conditions were found near the outlet (FIGS. 9(b)-9(c) and 9(e)-9(f)) and where surface curvature was large (see FIGS. 9(a) and 9(d)). Maximum of the maximum principal stress distribution (Stress-$P_1$) from FIG. 9(b) is 33 times higher than that from FIG. 9(e). Maximum Strain-$P_1$ (maximum principal strain) from FIG. 9(c) is almost 3 times of the maximum Strain-$P_1$ value from FIG. 9(f). The large variation of stress/strain values indicates that there is a large amount of information contained in the stress/strain distributions with the potential to be used for mechanical analysis of patch design and RV function analysis. The locations of maximal stress/strain conditions are mainly associated with large geometry curvatures which indicate the importance of accuracy of MRI technology.

A sketch of a diseased RV with scar tissue and patch (FIG. 5(a)) and two computational patch models were shown in FIGS. 5(a)-5(c). In the computational model, the patch material was made 10 times stiffer (by adjusting $c_1$ and $D_1$ values) than the RV muscle material. The results indicated that flow patterns and pressure distributions in the patched RV were similar to that in the RV without patch, with reduced total RV volume variations. FIGS. 10(a)-10(d) give Stress-$P_1$ and Strain-$P_1$ distributions obtained from the patched FSI model with the large patch indicating that the maximum of Stress-$P_1$ on the cut-surface is about 37% lower than that from the RV without patch. Maximum Strain-$P_1$ is also slightly lower (about 5% lower). The stress/strain maximal values occurred at locations with large curvatures. These results indicate that the maximum-value approach may not lead to critical information needed to analyze the effects of a patch on RV function and mechanical conditions. Methods more sensitive to patch addition and shape variations are needed to perform mechanical analysis for RV function and obtain critical information useful for surgical planning and patch design.

Using a critical site tracking (CST) method introduced in the atherosclerotic plaque mechanical analysis and assessment (Tang et al., 2004, see above; Tang et al., 2005, see above), the present inventor turn attention to local stress/strain behaviors in the patch area which is clearly more relevant to the design and optimization. This CST method reduces the 3D data mining to stress/strain analysis at selected sites and may be computationally essential in the process of identifying critical stress/strain information useful for the purpose. Six locations (see FIG. 11(a)) were selected to track stress/strain variations, with four sites located at the 4 sides of the patch (X1–X4), and one site at the center of the patch (X5), and one site near the maximum Strain-$P_1$ location (X6). FIGS. 11(a)-11(e) give Stress-$P_1$ and Strain-$P_1$ tracked at the 6 designated sites from the no-patch model and the patch model (large patch) over a cardiac cycle providing local stress/strain behavior. Differences in stress/strain variations at different locations can be as much as 1000% (10 times) in one cardiac cycle giving rich information for RV and patch analysis and assessment. Stress/strain behaviors are closely related to RV geometry; and valve locations, patch size, location and stiffness parameters. However, the clinical significance of these results needs to be investigated through larger-scale patient studies.

Figure 12:
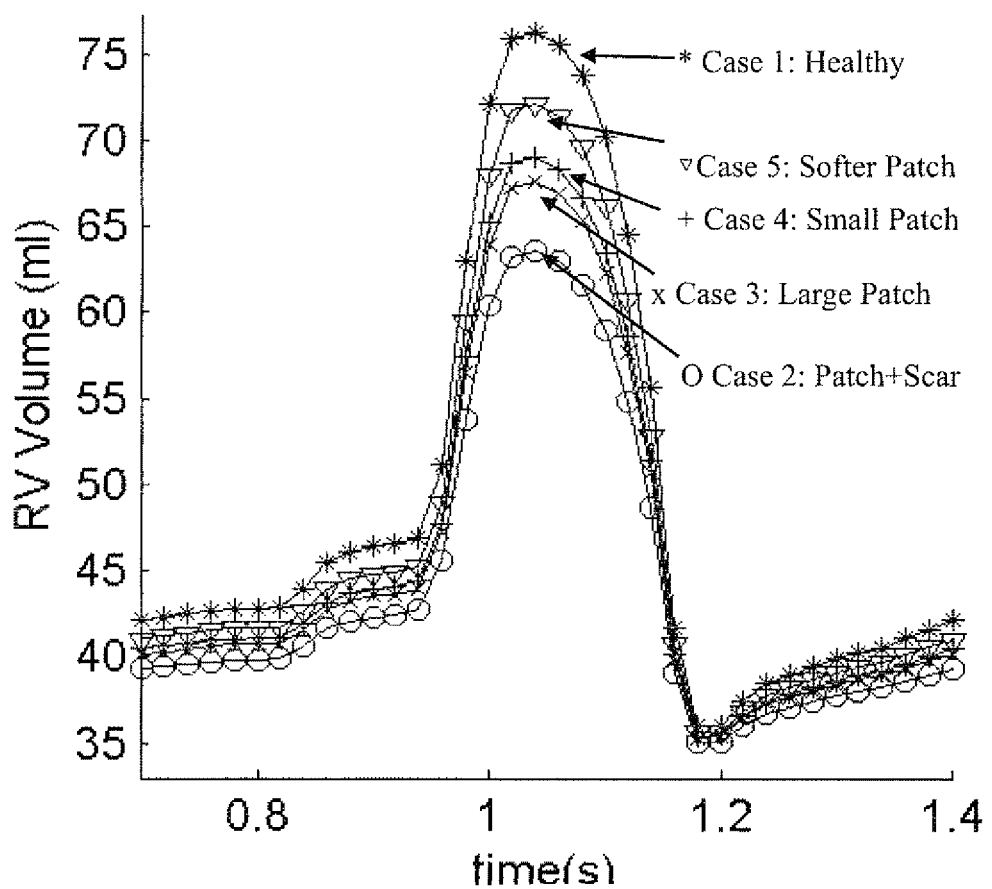
FIG. 12 is a graph comparison of RV volumes for 5 cases showing patches with matching material properties and smaller size lead to higher stroke volume and better RV ejection fraction (EF) recovery.

The main function of the heart is to pump blood to the human body. Two major measures of RV functions are SV and EF defined as:

$$SV = \text{RV End Diastolic (maximal) Volume} - \text{RV End Systolic (minimal) Volume}, \quad (9)$$

$$EF = (RVEDV - RVESV)/RVEDV, \quad (10)$$

where RVEDV=RV end diastolic volume and RVESV=RV end systolic volume. Simulations were conducted for 5 cases with variations in patch geometry and stiffness to investigate their effects on RV function as follows: Case 1 provided the baseline model without a patch and the healthy RV. Case 2 provided the RV with scar tissue and old patch as shown by FIG. 5(a) (illustrative) representing the diseased RV needing surgery. Patch and scar stiffness were chosen to be 10 and 5 times of that of RV tissue, respectively. Scar tissue material was made stiffer reflecting its loss of contractibility. Case 3 provided an RV with a new patch (FIG. 5(b)). Case 4 provided an RV with a smaller patch (FIG. 5(c)). Case 5 provided an RV with a softer patch better matching RV tissue compliance, patch shape is the same as in Case 2, and patch stiffness is only 2 times stiffer than RV tissue. SV, EF values and their relative improvements with different patches are listed in Table 1. The time-dependent RV volume curves for the 5 cases are compared in FIG. 12.

TABLE 1

Comparison of EF and SV for five cases considered.

| Cases considered: | Case 1 Normal Tissue | Case 2 Scar + old Patch | Case 3 New Patch | Case 4 Small Patch | Case 5 Soft Patch |
|---|---|---|---|---|---|
| Ejection Fraction | 52.7 | 44.9 | 47.7 | 48.6 | 50.5 |
| FT Recovery | 100% | 0% | 35% | 49% | 72% |
| Stroke volume (ml) | 39.7 | 28.5 | 32.2 | 33.5 | 36.4 |
| SV Recovery | 100% | 0% | 33% | 45% | 71% |

The results indicate that the healthy RV has the highest SV and EF, followed by the soft patch, small patch, the large patch case, and the pre-operative case with scar tissue/patch. From these computations the present inventor concluded that RV patch of smaller size and material compliance closer to RV tissue leads to greater improvements in RV function. The soft patch resulted in an impressive 72% EF and 71% SV relative recovery rate, respectively. These results (verifiable by MRI data) provide clear measurement of critical RV function indices, and give initial evidence that the proposed surgical procedures and modeling approach may lead to realistic improvement of RV cardiac function following RV remodeling surgery. The results should be interpreted very carefully with consideration given to the FSI model assumptions.

Example 3

Computational Simulations for Optimal Surgical Procedures and Patch Design

RV/LV morphology, pressure conditions and flow rate in the inflow and outflow regions are acquired from patients prior to pulmonary valve replacement and RV remodeling surgeries. All the geometrical data is entered into the ADINA system, pixel by pixel. Then computational lines, surfaces, and volumes are created under the ADINA environment to generate the computational mesh and finite element model. Fluid domain is created using the RV inner surface as the FSI interface. Valve positions are determined based on flow data quantified from CMR. The full FSI model is given by equations given above. The fully-coupled FSI RV/LV combination model is then solved by ADINA to obtain full 3D flow, deformation and stress-strain solutions which serve as the basis for mechanical analysis of the present invention, RV cardiac function analysis, surgical procedure design and patch optimization.

Figure 13A:
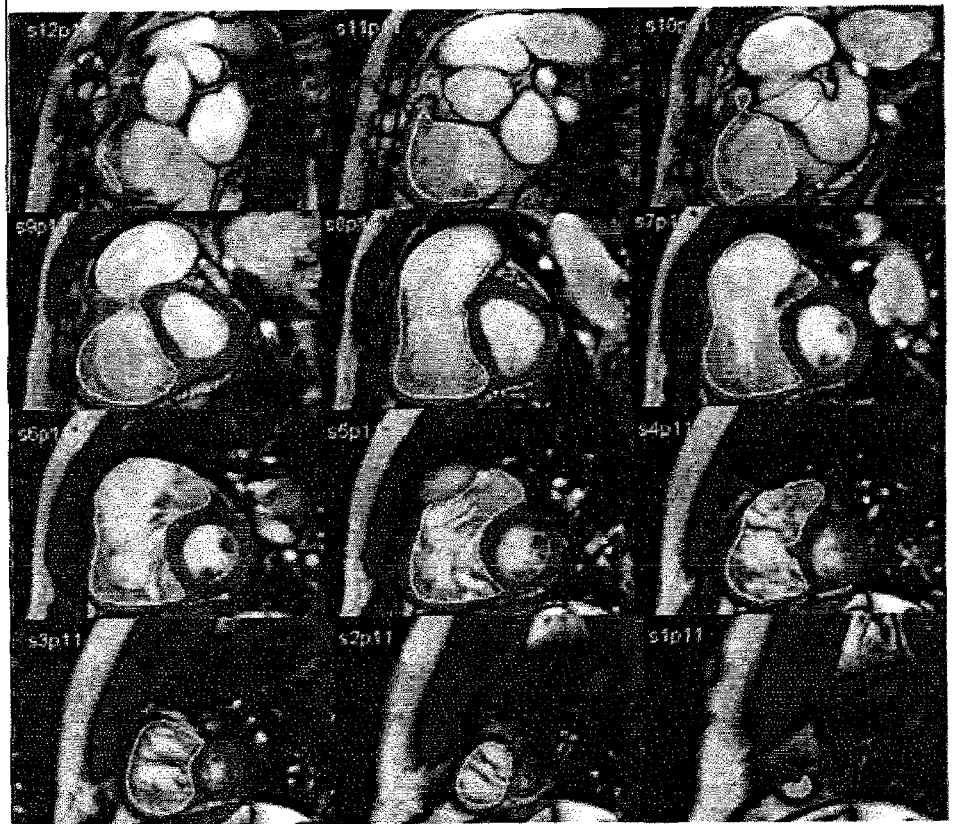
FIG. 13(a) is pre-operation cardiac magnetic resonance (CMR) images (end-systole) acquired from a patient.
Figure 13B:
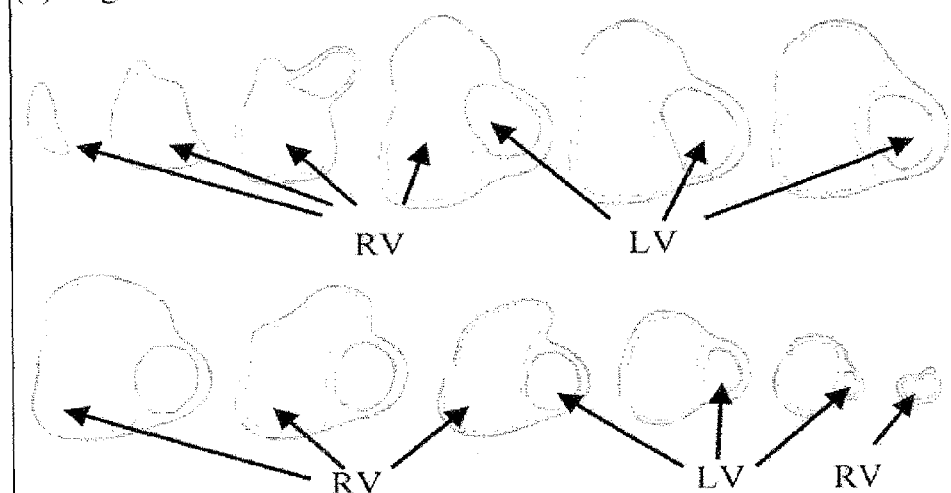
FIG. 13(b) is segmented RV/LV contours for model construction of the present invention.

FIGS. 13(a)-13(b) give a set of pre-operation end-systole cardiac magnetic resonance images from a patient and segmented RV/LV contours (MASS®). 3D images were acquired for 30 time-points in one cardiac cycle. The 3D image set for each time point consists of 12-14 2D images which are segmented to get RV/LV contours. It is noted that the RV from this patient is much larger than the healthy RV given in FIGS. 2(a)-2(e). FIGS. 13(a)-13(b) show the reconstructed 3D geometry of the RV and LV showing the contours, RV/LV inner surfaces, and RV/LV outsurface with valve positions. The old patch and scar were marked (FIG. 14(d)) based on the delayed enhancement CMR and experience of the cardiologist, and verified during surgery. The inflated RV/LV shape under maximum pressure is given by FIG. 14(e), with maximum principal strain distribution shown by shading.

Figures 15A, 15B, 15C, 15D:
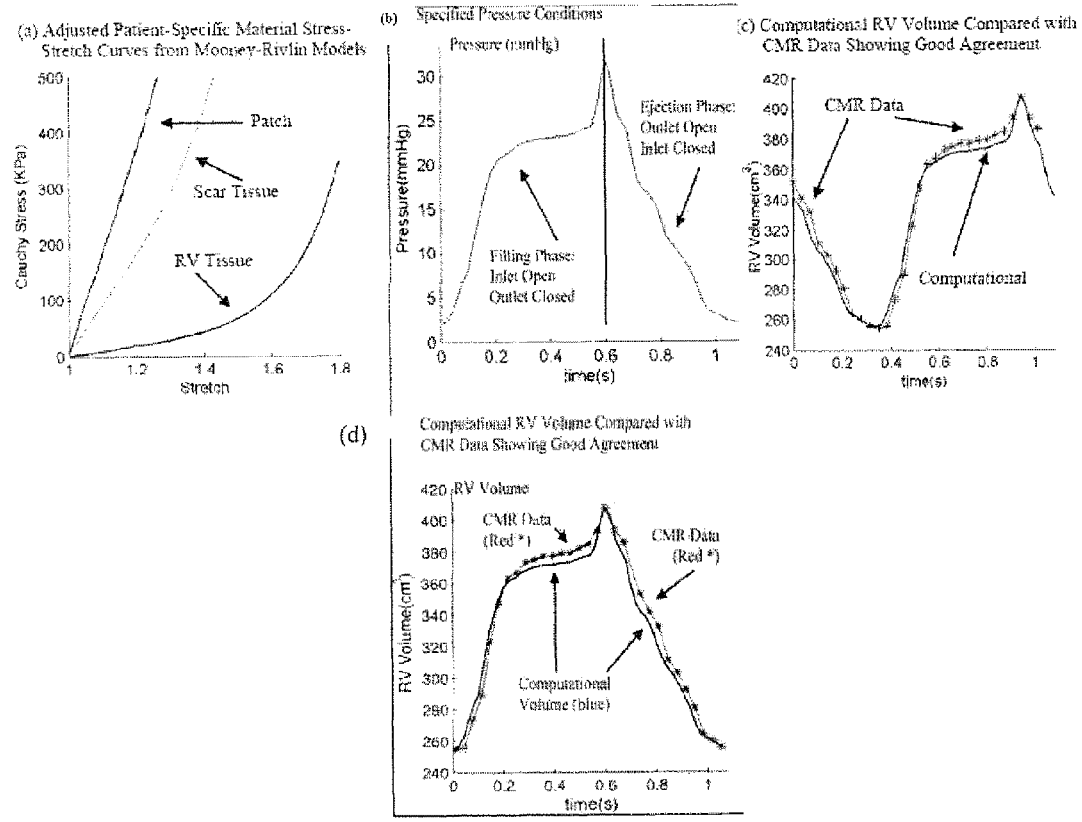
FIGS. 15(a)-15(b) are graphs showing adjusted patient-specific material stress-stretch curves from Mooney-Rivlin models for ventricle tissue, scar and patch materials, and specified pressure conditions, respectively.
FIGS. 15(c)-15(d) are graphs showing computed RV volume compared with CMR recorded data showing good agreement (error margin <3%).

With patient-specific pressure and RV volume data, parameters in the modified Mooney-Rivlin model were selected so that a good agreement between computational results and CMR measured data was reached. FIGS. 15(a)-15(c) show the material stress-stretch curve, pressure conditions used in the model and the matched volume curves. The maximum error (from the 30 time points where MRI data is available) is an impressive 2.7% (11.1 ml/406.9 ml end of diastole), well within the measurement accuracy margin. These patient-specific data lead to improved predicting power of models of the present invention.

Figures 16A, 16B, 16C, 16D, 16E:
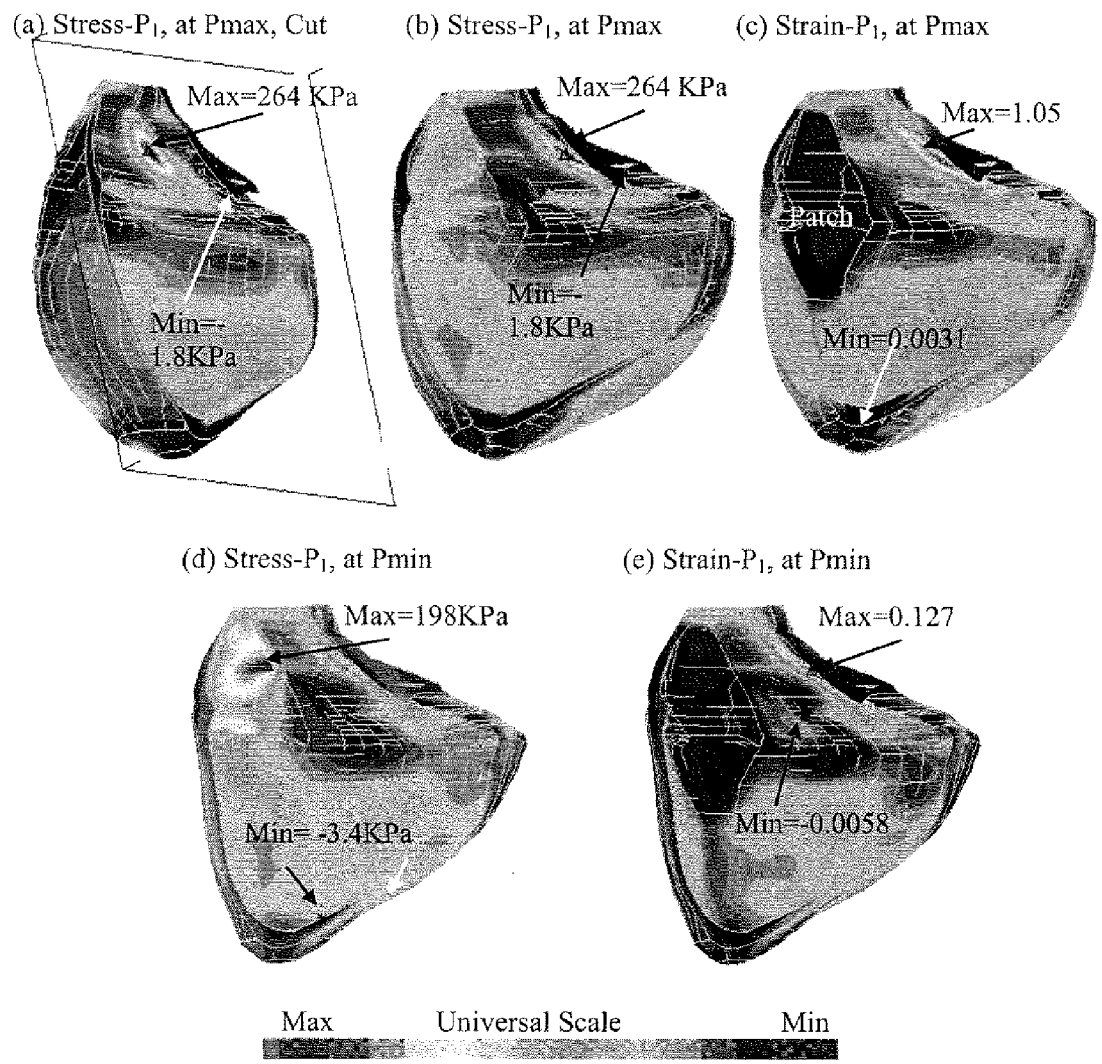
FIGS. 16(a)-16(e) are schematic views showing selected cut-surface and Stress-$P_1$ and Strain-$P_1$ corresponding to maximum and minimum pressure conditions.
Figures 19A, 19B, 19C, 19D, 19E, 19F, 19G, 19H, 19I:
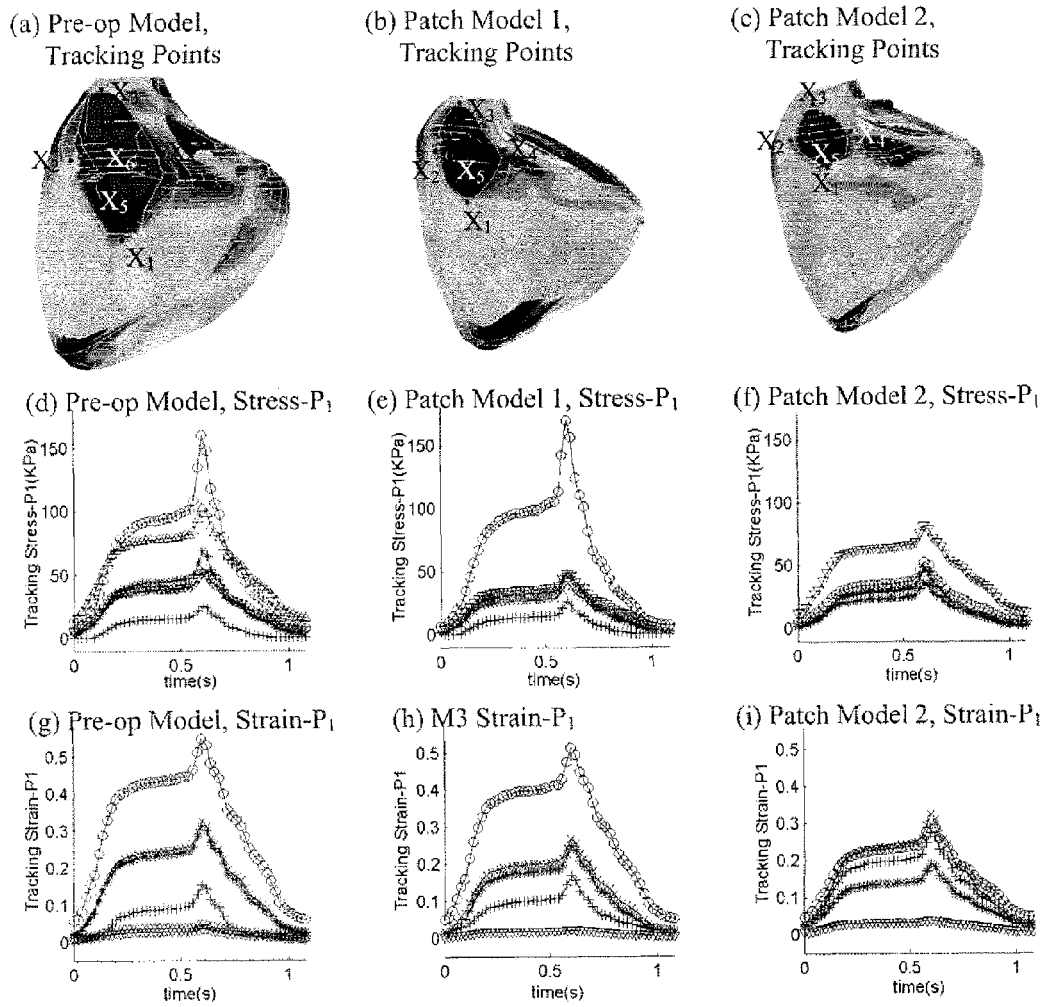
FIGS. 19(a)-19(i) show Stress-$P_1$/Strain-$P_1$ variations tracked at selected locations for three cases, which show that stress/strain levels (around the patches) are considerably lower (50% for stress, 40% for strain) from Patch Model 2 to the other two models.

A cut-surface and stress/strain distributions are given by FIGS. 16(a)-16(e). Maximum stress values are found to be closely related to RV curvature and wall thickness, less influenced by stiffness variations. Maximum principal strain distributions demonstrated a closer link to stiffness changes, as shown by FIGS. 16(c) and 16(e). Flow velocity and pressure patterns are similar to those shown FIGS. 7(a)-7(d) and 8(a)-8(d) and are omitted here. Stress/strain behaviors will be presented and compared when all the patch models are presented below in FIG. 19.

Figures 17A, 17B, 17C:
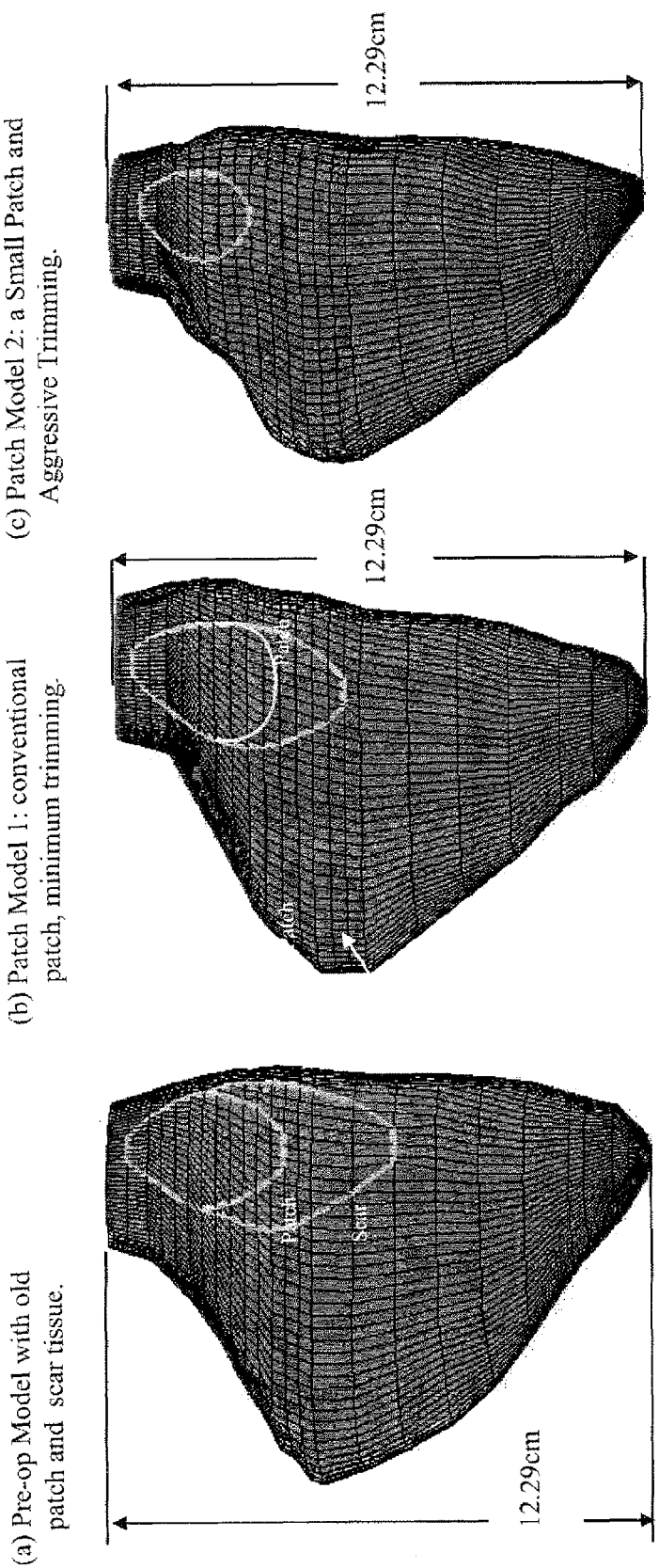
FIGS. 17(a)-17(c) are sketches of models with different patch designs: (a) Pre-operation model with the old patch and scar tissues; (b) Patch Model 1 (as indicated in the flow chart of FIG. 1) with a conventional patch and minimum scar tissue trimming; (c) Patch Model 2 (see flowchart) with a Small Patch and Aggressive Trimming.

Using the pre-operative data from each patient and guidance from surgeons, three patch models are constructed (see FIGS. 17(a)-17(c)). The first patch model is a pre-operation model (FIG. 17(a)). The pre-operation model contains the old patch and scar tissues with a pulmonary valve inserted. This would mimic catheter based percutaneous pulmonary valve insertion. The second patch model, "Patch Model 1" (conventional patch, called large patch or patch 1), includes a new smaller patch replacing the old patch plus a pulmonary valve replacement (PVR). The third patch model, "Patch Model 2" (the proposed new patch, called small patch or patch 2) includes a new patch (smaller) and scar tissues removal plus a PVR. Additional models (model 3 as indicated in the flow-chart of FIG. 1) and simulations are performed to optimize the patch design with selected parameters, subject to surgical and other technical constraints.

Figure 18A:
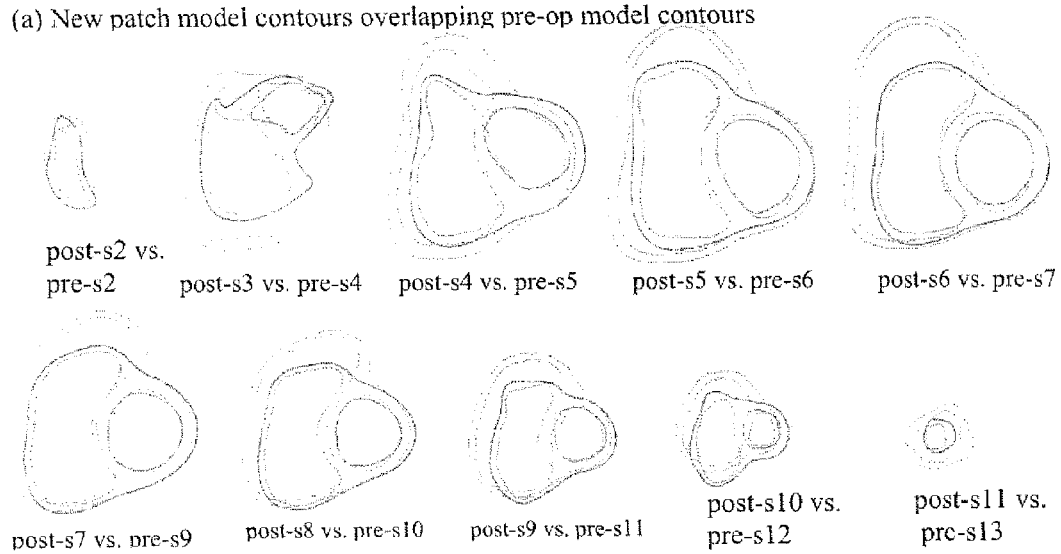
FIGS. 18(a)-18(b) are illustrations of the model optimization procedures of the present invention: (a) Overlapping contours of the pre-operation model and Patch Model 2 showing RV reduction at contour level; (b) Overlapping contours of one slice from three models given in FIG. 17 showing the model differences. For better illustration, contours from actual post-operation CMR images of the same patient were used as Patch Model 2 contours.
Figure 18B:
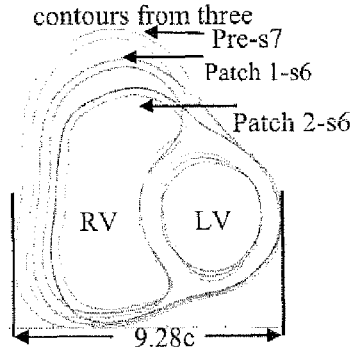

FIGS. 18(a)-18(b) give overlapped contour plots of the pre-op and "target" models and one sample of overlapped contours from the three models given by FIGS. 17(a)-17(c). To better illustrate the process, contours from actual postoperation (post-op) CMR images of the same patient are used as the target contours in FIGS. 18(a)-18(b), while in realty they are unknown at the time of patch design. Experience on the part of the cardiologist plays an important role in determining the "target" RV morphology in the design process, while computational results provide quantitative numbers supporting the proposed surgical procedures.

After the models are solved, solutions are compared and analyzed. Model geometry and patch design are adjusted to optimize the predicted post-operation RV cardiac functions. FIGS. 19(a)-19(i) give Stress-$P_1$/Strain-$P_1$ variations tracked at selected locations for the three cases showing that stress/strain levels around the patch are considerably lower (50% lower for stress, 40% lower for strain) from the small patch model compared to the other two models. RV volume variations of the three models have similar patterns mostly determined by the specified pressure conditions (see FIGS. 15(a)-15(c)). RVEDV, RVESV, SV and EF values for the three models are summarized in Table 2 which indicates that the proposed small patch design would provide about 10% improvement in EF, compared to the conventional surgical procedures (38.5% versus 35.3%). The EF improvement is more than 100% compared to the pre-op ventricle, when PR is taken into consideration (38.5% versus 18.3%; see below). As part of the RV remodeling clinical trial by T. Geva (see above) the patient was randomized to either conventional patch reduction plus a PVR, or RV remodeling with patch reduction, scar tissue removal, plus a PVR.

TABLE 2

Summary of stroke volume and ejection fraction from 3 models showing that the proposed small patch model improved EF by about 10% compared to the conventional procedures, and more than 100% compared to the pre-op ventricle, when PR is taken into consideration.

| Cases considered: | Pre-Op Model Old Patch + Scar | Pre-Op Model +Pulmonary Regurgitation | Patch Model 1 New Model Large Patch | Patch Model 2 New Model Small Patch | CMR-Data Post-Op actual data | Model 2 modified Using post-operation data |
|---|---|---|---|---|---|---|
| RVEDV (ml) | 408.5 | | 255.8 | 206.0 | 188.3 | 190.2 |
| RVESV (ml) | 255.4 | | 165.6 | 126.7 | 115.0 | 115.5 |
| SV | 153.1 | 74.6 (outflow) | 90.2 | 79.3 | 73.3 | 74.7 |
| Ejection Fraction (%) | 37.5 | $EF_{PR-adj}$ 18.3 | 35.3 | 38.5 | 38.9 | 39.2 (over estimate) |

PR seriously affects RV cardiac function and should be taken into consideration when assessing RV ejection fraction before surgery to obtain true improvement in EF after surgery. For the case considered (FIG. 17(a)), CMR-measured averaged flow-rate and accumulated out-flow volume at the pulmonary valve are given by FIGS. 20(a)-20(b). Total recorded outflow in one cardiac cycle is 159.63 ml; pulmonary regurgitation: 81.83 ml; PR rate: 51.26%; net outflow: 74.6 ml. When pulmonary regurgitation is combined in the calculation, the EF improvement of the proposed patch model is more than 100% compared to the pre-operation model (see Table 2). The PR-adjusted ejection fraction ($EF_{PR-adj}$) given by $$EF_{PR-adj} = (RVEDV - RVESV - PR\ volume)/RVEDV. \quad (11)$$

provides a more accurate measure of RV functions and was used in Table 2.

There are several types of patch material with different degrees of elasticity (Dacron, PTFE, bovine pericardium, autologous pericardium, etc.). Material parameters in the patch models are adjusted according to industrial specifications to quantify effects of patch material properties on RV function recovery (Dang, A. B., Guccione, J. M., Zhang, P., Wallace, A. W., Gorman, R. C., Gorman III, J. H., and Ratcliffe, M. B., 2005, "Effect of Ventricular Size and Patch Stiffness in Surgical Anterior Ventricular Restoration: A Finite Element Model Study," Ann. Thorac. Surg., 79(1), pp. 185-193).

Since there are many factors involved and model construction is very time consuming and labor-intensive, an incremental adjustment approach is followed, subject to surgical and anatomical constraints, and with guidance from the surgeon. Starting from the current most conservative patch model 1 (minimum to no removal of scar tissue and a conventional patch) to the most aggressive patch model 2 (maximum resection surgically possible and safe of scar and patch), a middle-ground model (see Model 3 in FIG. 1) is designed based on patient-specific anatomy, blood pressure, and other relevant factors. Results from the three models are presented to the surgeon after the surgery for his review. When postoperation data is obtained, model adjustments are made as needed to optimize the predicted outcome (see Table 2). Experience learned from analyzed cases may be applied to new cases so that factors such as RV remodeling and pressure adjustment after surgery can be included in the model design for more accurate predictions. Preliminary results indicate that the small patch model (patch model 2) leads to improved RV function recovery and lowered stress/strain variations which may also be helpful for the ventricle to save energy and improve its function. More studies are needed to validate these initial observations.

Standard statistical analysis is performed to quantify possible correlations between model parameters (RV morphology, pressure, degree of trimming, patch size) and model predictions (SV and EF) and correlations between model predictions and actual post-operation data (six-month post-operation follow-up). One long-term goal is to build up experience and database so that eventually a software can be made which will give predictions for key RV function indices (SV, EF) with input of model parameters and specifications (e.g., long and short RV axes, maximum RV pressure, RV ESV, RV EDV, and others to be identified by research) without constructing and solving the full 3D models. The software will be backed by sophisticated 3D model calculations and large-scale patient study database which lend predicting power to such a simplified approach.

For this project it is anticipated that 25 ToF patients undergoing surgery will be required for the model development and validation. This number is based in part on the expected variability in patient RV size and structure as well as the expected range of values that the RV tissue compliance parameters will have in the different patients.

Example 4

Patient-Specific MRI-Based 3D FSI RV/LV/Patch Models for PVR Surgery and Patch Optimization A patient-specific RV/LV/patch combination model with FSIs was introduced to evaluate and optimize human PVR/insertion surgical procedure and patch design. CMR imaging studies were performed to acquire ventricle geometry, flow velocity, and flow rate for healthy volunteers and patients needing RV remodeling and PVR before and after scheduled surgeries. CMR-based RV/LV/patch FSI models were constructed to perform mechanical analysis and assess RV cardiac functions. Both pre- and postoperation CMR data were used to adjust and validate the model so that predicted RV volumes reached good agreement with CMR measurements (error <3%). Two RV/LV/patch models were made based on preoperation data to evaluate and compare two PVR surgical procedures: (i) conventional patch with little or no scar tissue trimming, and (ii) small patch with aggressive scar trimming and RV volume reduction. The modeling results indicated that (a) patient-specific CMR-based computational modeling can provide accurate assessment of RV cardiac functions, and (b) PVR with a smaller patch and more aggressive scar removal led to reduced stress/strain conditions in the patch area and may lead to improved recovery of RV functions (del Nido, P. J., 2006, "Surgical Management of Right Ventricular Dysfunction Late After Repair of Tetralogy of Fallot: Right Ventricular Remodeling Surgery," Semin. Thorac. Cardiovasc. Surg. Pediatr. Card. Surg. Annu., 2006, pp. 29-34).

Described herein is a novel integrated surgery/modeling process, which combines innovative surgical procedures, noninvasive CMR techniques, and computational modeling to optimize surgical techniques for RV anterior wall volume reduction and remodeling related to PVR. This approach is truly interdisciplinary where novel cardiac surgical procedures, CMR techniques, and advanced computational modeling are combined to optimize patch design and RV volume reduction methods for realistic clinical and surgical applications. Preoperation patient-specific RV/LV morphology, pressure, and adjusted material properties can be used to construct the model to predict postoperation outcome and model predictions can be verified by postoperation CMR measurements. The FSIs included in the FSI model can give both flow velocity, shear stress, and structural stress/strain distributions, which can serve as basis for many further investigations. Details of the RV/LV/patch combination model are given below.

Models and Methods

Data Acquisition and 3D Geometry Reconstruction

Figure 14A:
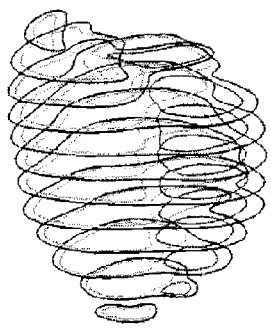
FIGS. 14(a)-14(e) are schematic views showing re-constructed 3D geometry of RV and LV, which show valve and patch positions.
Figure 14B:
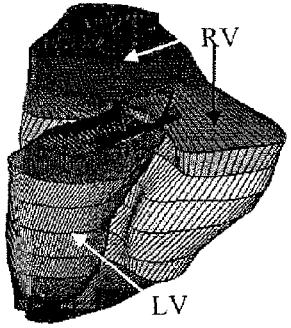
Figure 14C:
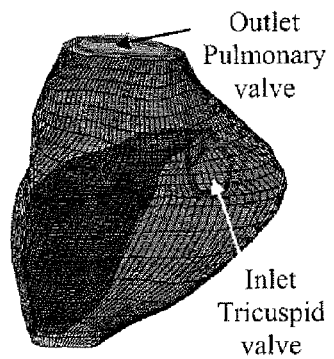
Figure 14D:
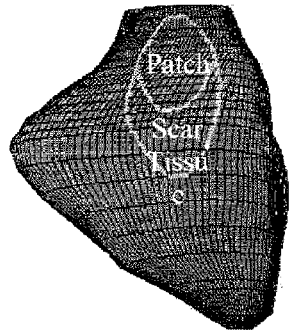
Figure 14E:
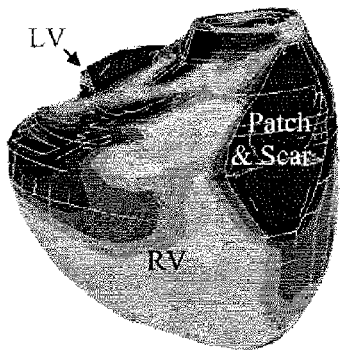

CMR studies were performed by Dr. Tal Geva in a dedicated MRI suite located in the Department of Cardiology at Children's Hospital (Boston, Mass.) to acquire patient-specific ventricle geometry, morphology, heart motion, flow velocity, and flow rate for patients needing RV remodeling and PVR operations before and after scheduled surgeries and healthy volunteers. Thirty RV/LV positions were acquired during one cardiac cycle. Each position contains 10-14 planar slices. 3D RV/LV geometry and computational mesh were constructed under the ADINA computing environment following known procedures (Tang et al., 2005, see above; Tang et al., 2006, see above; Yang et al., 2007, see above). The procedure is explained as follows. For each object (made of one material) such as the ventricle, patch, scar, or the fluid domain, its geometry was first divided into enough volumes so that each volume has a more regular shape for mesh/element generation. Next, an element group for each volume was specified, which includes element style, material, and other information (such as indications assuming large strain or large displacement for the kinematic formulation for the element group). After that, mesh density and mesh style were specified for each volume. Elements of all the volumes were generated using the ADINA command "Gvolume." The key here is the proper division of each physical object into computational volumes so that mesh/elements can be generated. This step has a strong influence on the element shape and convergence of the model. For a RV/LV/patch/scar combination model, many volumes are needed. FIGS. 14(a), 14(b) and 14(d) give the stacked MRI contours and RV/LV inner/outer surface plots showing patch, scar, and valve positions. The location and sizes of the patch and scar tissues were determined by del Nido with his experience and confirmed during actual surgery. Volumes and elements used for this patient-specific model are as follows: normal RV/LV tissue: volumes: 223, elements: 18,896; scar: volumes: 18, elements: 1020; patch: volumes: 11, elements: 880; and fluid: volumes: 138, elements: 152,591. Total volumes for the whole model: 390; total elements: 173,387.

Solid Model

The RV and LV materials were assumed to be hyperelastic, anisotropic, nearly-incompressible and homogeneous. Scar tissue and patch material were assumed to be hyperelastic, isotropic, nearly-incompressible and homogeneous. The governing equations for the structure models are gives in Example 2 above as Equations (1) and (2). Equations (1) and (2) are used for RV/LV muscle, patch, and scar tissues, with parameter values in the constitutive equations (given below) adjusted for each material. The strain energy function for the modified Mooney-Rivlin model, the 3D stress/strain relations, and the uniaxial stress/stretch relation for an isotropic material can be obtained from Equations (3)-(6) in Example 2 above. The patient-specific stress-stretch curves derived from Money-Rivlin models fitting CMR-measured data are given in FIGS. 3 and 15(a). Patch and scar stiffness were chosen to be 20 and 10 times of that of RV tissue, respectively (by adjusting c1 and D1 values, D2 was unchanged) so that they were considerably stiffer than RV tissues.

Fluid Model

Blood flow was assumed to be laminar, Newtonian, viscous, and incompressible. The Navier-Stokes equations with ALE formulation were used as the governing equations. Pressure conditions were prescribed at the tricuspid (inlet) and pulmonary (outlet) valves (See FIGS. 4(a)-4(d); Beme et al., 2004, see above; Kuehne et al., 2004, see above). Since RV muscle was treated as a passive material, pressure conditions were modified so that RV could be inflated properly by fluid forces (FIGS. 4(a)-4(d)). No-slip boundary conditions and natural force boundary conditions were specified at all interfaces to couple fluid and structure models together (Bathe, 2002, see above; Bathe, 1996, see above). Putting these together, we have $$p(\partial u/\partial t+((u-u_g)\cdot \nabla)u)=-\nabla p+\mu \nabla^2 u \quad (12)$$

$$\nabla \cdot u=0 \quad (13)$$

$$u|_\Gamma=\partial x/\partial t, \partial u/\partial n|_{inlet,outlet}=0 \quad (14)$$

$$P|_{inlet}=p_{in}(t)(\text{inlet open}), u|_{inlet}=0(\text{inlet closed}) \quad (15)$$

$$P|_{outlet}=p_{out}(t)(\text{outlet open}), u|_{outlet}=0(\text{outlet closed}) \quad (16)$$

$$p|LV=pLV(t) \quad (17)$$

$$\sigma_{ij}\cdot n_j|_{out\_wall}=0 \quad (18)$$

$$\sigma^r_{ij}\cdot n_j|_{interface}=\sigma^s_{ij}\cdot n_j|_{interface} \quad (19)$$

where u and p are fluid velocity and pressure, $u_g$ is mesh velocity, F stands for RV inner wall, $f \cdot_j$, stands for derivative of f with respect to the jth variable, and u is structure stress tensor (superscripts r and s indicate different materials: fluid, RV tissue, scar, and patch). Together with equations (1)-(3) we have the completed FSI model.

The simulation cycle was started when RV has its smallest volume (end of systole) corresponding to the minimal inlet pressure. As the inlet pressure increases (inlet is kept open), blood flows into RV and its volume increases. When RV reaches its maximal volume, the inlet closes and the outlet opens. Blood is ejected and RV volume decreases. That completes the cycle. While the mechanism driving the motion is different from the real actively contracting heart, the simulated RV motion, deformation, volume change, and fluid flow can provide results matching patient-specific data with properly adjusted material parameters and flow-pressure boundary conditions.

LV Model

LV model was obtained by essentially the same way as previously described in Example 2.

Results

Results From a Healthy RV Case

A healthy case (FIGS. 2(a)-2(e)) provided some base line information. The fully coupled FSI RV/LV model was solved by ADINA (ADINA R&D, Watertown, Mass.) to obtain full 3D flow, deformation, and stress-strain distributions, which served as the basis for the investigations. Pressure conditions given in FIG. 4(c) were prescribed. FIGS. 22(a)-22(d) give maximum principal stress (Stress-$P_1$) and maximum principal strain (Strain-$P_1$) plots with a cut surface chosen so that stress/strain behaviors on the RV inner surface could be observed. Maximum Stress-$P_1$/Strain-$P_1$ values were observed near the RV outlet where RV curvature was large. FIGS. 7(a)-7(d) give four flow velocity plots at different fillings and ejection times, which show interesting patterns with multiple vortexes. The implications of these complex flow velocity and shear stress patterns on RV cardiac functions and disease development will be investigated when more patient data become available. Further solution details are omitted because the focus is on surgical optimization for diseased RVs in this paper and more results will be reported in the following sections.

Diseased RV Case Based on Preoperation Data

With experience learned from the healthy case, a RV/LV/patch model based on preoperation data from a patient was constructed (FIGS. 13(a), 13(b), 14(a), 14(b) and 14(d)) and solved by ADINA. It should be noted that the diseased RV is considerably larger than the healthy one. This model (M1) would be validated by preoperation data and used to create new patch models to evaluate various surgical and patch options. FIGS. 15(b)-15(c) show the prescribed pressure conditions and an impressive agreement between the computational and CMR-measured preoperation RV volumes achieved by adjusting material parameters and prescribed pressure conditions in the model. FIGS. 16(a)-16(d) give the position of a selected cut surface and Stress-$P_1$/Strain-$P_1$ distributions on the inner RV surface corresponding to maximum/minimum pressure conditions. Once again, maximum Stress-$P_1$/Strain-$P_1$ values occurred at locations with large curvatures. The patch and scar areas had lower strain values (FIG. 16(c)) because the materials were stiffer, as expected.

Patch Design and Surgical Options, RV Cardiac Function Assessment

With the model tuned using the patient-specific preoperation material and pressure data (the volume agreement could be considered as validation by the preoperation data), new patch models could be made to evaluate different patch designs and surgical options. FIGS. 17(a)-17(c) give sketches of three models: the preoperation model (M1), Patch Model 1 (M2, conventional), and Patch Model 2 (M3, small patch with aggressive trimming). Patch Models M2 and M3 were designed with guidance from del Nido, a cardiac surgeon with more than 20 years of surgical experience. Each slice from the M1 model was shrunk to get the corresponding slices for M2 and M3 and desirable volume reductions. The slices and reconstructed geometries of M2 and M3 were reviewed by del Nido and adjusted as needed before they were used to build the FE models. FIGS. 18(a)-18(b) illustrate how M2 and M3 were constructed from the original M1 contours. With the newly designed patches and RV geometries, the models were solved by ADINA and solutions were compared and analyzed.

Results reported above indicated that global maximum stress/strain values often occur at locations with large curvatures; therefore, they may not be good indicators for model/patch comparison and optimization purpose. previous experiences from Tang, et al., 2005 (see above) suggest that stress/strain variations at selected locations near the patch may be more sensitive indicators for model comparisons. FIGS. 19(a)-19(i) give Stress-$P_1$/Strain-$P_1$ variations tracked at selected locations in the patch area for the three cases showing that stress/strain levels around the patch are considerably lower (50% lower for stress and 40% lower for strain) from the small patch model compared to large patch models. This means that the smaller patch would be under lower stress conditions and the ventricle with a smaller patch would not have to work as hard as the ones with larger patches. The significance of this finding needs to be supported by further clinical studies.

To assess RV cardiac functions and evaluate possible outcome of different surgical options, two commonly used measures of RV functions (Equations (9) and (10)) were used. Results indicated that while maximum RV volumes for the three models were different as expected, their volume variations in a cardiac cycle had similar patterns mostly determined by the specified pressure conditions (see FIGS. 15(b) and 15(d)).

Discussion

Model Selection and Limitations

The model herein is a first attempt to introduce patient-specific RV/LV/patch/scar combination models with FSIs for realistic computer-aided surgical design and optimization. Several simplifications were made when the model was selected: Active heart contractions, fiber orientations, and anisotropic properties were not included in model. These model simplifications were made for the following reasons: (a) it is desirable to use clinically measurable data so that the model can be used in patient-specific surgery design and realistic clinical applications, (b) the model should be simple enough to be constructed and solved for a quick turnaround time (ideally within 24-48 h when implemented for clinical use), and (c) the model should capture key factors so that one can assess RV cardiac function (right ventricle SV and EF) and make accurate and verifiable predictions needed in the surgery design. Since material parameters can be adjusted so that model-predicted RV volumes can match CMR-measured RV volumes (which can be considered validation by patient data), the model can be used for accurate RV cardiac function assessment based on SV and EF calculations. It should be understood that predicted stress distributions will be more model dependent and should be interpreted with caution. However, comparative stress studies can still provide useful information because relative differences will be less model dependent.

Several improvements can be added to the models described herein in the future for better accuracy and applicability: (a) Valve mechanics. Valves can be added into model for better flow control at the inlet and outlet. (b) Fiber orientation and anisotropic material properties (see Example 6). The measurement of patient-specific fiber orientation data is described in Example 6 below. Single and multilayered (epicardium, midlayer, and endocardium) anisotropic models can be introduced to seek possible improvement in computational prediction accuracies. (c) Active contraction model. One way to add active contraction into model is to introduce an external force field, which is tied to fiber structure and orientations. Measurement and validation of the external force field are not currently available. It is expected that the SV and EF predictions by the model described in this Example and a heart model including active contractions would again be at the same accuracy level. With the above discussions, it is reasonable to use the model described in this Example in RV remodeling optimization process. However, these models can be adjusted if necessary for further improvements. Another way to induce contraction is to make the RV material stiffer during systole. Compared with these improved models, it is expected that the SV and EF predictions by the model will have similar accuracies since calculation of SV and EF involves RV volumes and the improved models will also be adjusted to match CMR-measured data.

Patch Material Properties

The results described herein indicated that the best patch material would be materials that have similar elastic properties to that of ventricle tissues. This is limited by market availability.

Validation of the Commercial Finite Element Package

ADINA has been validated by many applications. The FSI artery models developed in the past several years have also been validated by in vitro experiments (Tang, D., Yang, C., Kobayashi, S., and Ku, D. N., 2004, "Effect of a Lipid Pool on Stress/Strain Distributions in Stenotic Arteries: 3D FSI Models," *J. Biomech. Eng.*, 126, pp. 363-370; Tang, D., Yang, C., Zheng, J., and Vito, R. P., 2003, "Effects of Stenosis Asymmetry on Blood Flow and Artery Compression: A Three-Dimensional Fluid-Structure Interaction Model," *Ann. Biomed. Eng.*, 31, pp. 1182-1193).

Example 5

Adjustment and Validation Using Pre- and Post-operative Patient-Specific Data

One advantage of the approach described herein is that postoperation data can be obtained to validate computational predictions based on preoperation data. When needed, the computational model can be adjusted to better match postoperation CMR measurements.

Pre-operation data (morphology, motion, pressure, and RV volume) were used not only for constructing the model described herein, but also for validation of the model and computational results. RV pressure and volume data were used to determine patient-specific material parameter values for material models to fit CMR RV volume data. Computer-simulated heart motion is compared with recorded heart motion by MRI and the model assumptions are adjusted for best fit. The validated model matching pre-operation data (patient-specific RV/LV morphology, material parameters and pressure conditions) are used to perform patch-design simulations and predict post-operation RV cardiac function. Since the model was applied to the same patient, the pre- and post-operation ventricle tissue material properties should remain the same. The validated model matching pre-operation data (patient-specific RV/LV morphology, material parameters, and pressure conditions) were used to perform patch-design simulations and predict post-operation RV cardiac function. The model (mainly the pressure condition) was adjusted again to match post-operation CMR-measured RV data for more accurate predictions. While the ventricles are the same (other than the patch and scar tissue removal), the flow mechanical environment is considerably different, which leads to pre- and post-operation RV pressure differences. More case studies will help better predict post-operation RV pressure prior to surgery so that the first-time prediction accuracy can be improved. In a way, the modeling process will "learn" to improve as more experience is gained.

Figure 23A:
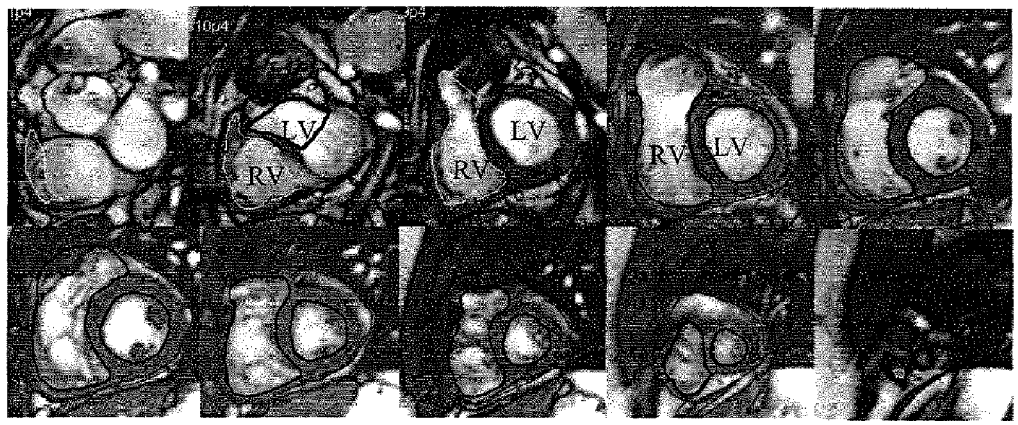
FIGS. 23(a)-23(c) show validation by post-operation data according to the present invention: (a) Post-operation CMR images; (b) Graph of computational pre- and post-operation pressure conditions in RV; (c) Comparison graph between measured RV volume and two computational predictions. Blue line: pressure and volume from Patch Model 2 prior to post-operative data (CMR max volume 188.3 ml, predicted volume 205.97, error margin 9.4%); black line: adjust pressure condition and improved RV volume prediction using post-operation data (new predicted volume 190.2, error <3%).
Figure 23B:
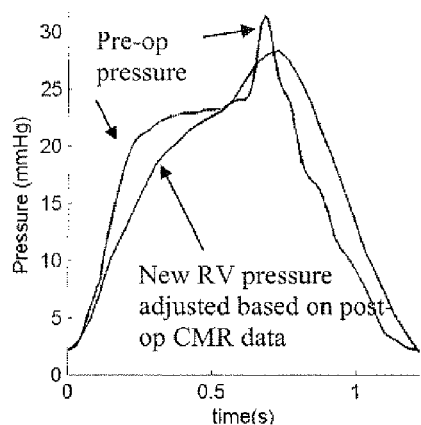
Figure 23C:
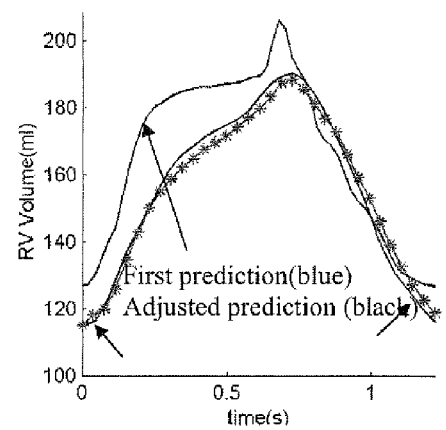

With as much preparation and optimization as one could do, actual surgery outcome may differ from computational predictions. After all, there is a considerable distance between computational models and what the surgeon can accomplish in the operating room. Follow-up data were acquired about six months after the surgery and compared with pre-operation computational predictions. This serves as validation of the proposed surgical procedure and optimization process and provides valuable information for future improvements. FIGS. 23(*a*)-23(*c*) give post-operation MR images of the same patient whose pre-operation data were used for the demonstration. The CMR-measured postoperation RV volume and computer-predicted RV volume based on preoperation data are given by FIG. 23(*b*). The error margin of volume predictions was 9.4%. The CMR-measured and computer-predicted (patch Model 2) RV volume curves are given by FIG. 23(*c*), and the error margin was 9.4%. Noticing the differences in the volume profile, the over-all over-estimation by Patch Model 2, and that it is the same patient with the same ventricle, pressure condition and material parameters were adjusted, with the prescribed pressure profile modified and the material parameters kept unchanged. The newly predicted RV volume had much improved accuracy (newly predicted maximum volume: 190.2 ml, error for the entire cycle <3%). RV cardiac functions (SV and EF) values are listed in Table 2 to compare with those from other models and actual post-operation CMR measurements. The EF for the modified small patch model was 39.2% (See Table 2). This modification technique will be applied to future cases so that the first-time prediction accuracy can be improved.

Velocity information at selected region of interest (inflow and outflow regions, flow rates, max/min velocity values) can be acquired by CMR and used for model validation purpose.

Example 6

Two-Layer Passive/Active Anisotropic FSI Models with Fiber Orientation: MRI-Based Patient-Specific Modeling of RV Response to Pulmonary Valve Insertion Surgery Early 3D models for blood flow in the heart include Peskin's model which introduced fiber-based LV model and the celebrated immersed boundary method to study blood flow features in an idealized geometry with FSIs (Peskin, 1975, see above; Peskin and McQueen, 1992, see above). The previous examples introduced FSI RV/LV/Patch combination models based on patient-specific MRI data with healthy and diseased RV to perform computational simulations for surgery design and patch optimization. While the isotropic FSI models were able to provide accurate RV volume predictions, it is well-known that heart ventricles have multi-layer structure and that heart muscle demonstrates clear anisotropic material properties. Computational predictions for heart deformation and stress/strain predictions could be improved if anisotropic material properties and fiber orientation could be included in the model.

A single-layer isotropic patient specific RV/LV/Patch combination model with FSI was introduced in the above examples to evaluate and optimize human PVR/insertion surgical procedure and patch design. In this example, an active anisotropic model with two-layer structure for ventricle wall and tissue fiber orientation was introduced to improve previous isotropic model for more accurate assessment of RV function and potential application in PVR surgery and patch design. A material-stiffening approach was used to model active heart contraction. The computational models were used to conduct "virtual (computational)" surgeries and test the hypothesis that a PVR surgical design with a smaller patch and more aggressive scar tissue trimming would lead to improved RV cardiac function recovery. Results from the models validated by pre-operation data indicated that the small patch design had 11% improvement in RV function as measured by RV ejection fraction, compared to the conventional patch. Maximum Stress-P1 value from the active anisotropic model was 121.2% higher than that from the passive isotropic model. Computational RV volume predictions agreed well with CMR-measured volume data (error <2%).

Recent advances in computational modeling, methods and computer technology have made it possible for computer-simulated procedures (virtual surgery) to be used in clinical decision making process to replace empirical and often risky clinical experimentation to examine the efficiency and suitability of various reconstructive procedures in diseased hearts. Since FSI definitely plays an important role in heart motion and mechanical and cardiac functions, isotropic RV/LV/Patch combination models with FSIs were introduced (see the Examples above) to evaluate RV cardiac function and provide helpful mechanical flow and stress/strain analysis for surgical procedure and patch design. In this Example, anisotropic material properties, a two-layer ventricle structure with tissue fiber orientation, and a material-stiffening approach to model active heart contraction were added to the RV/LV/Patch FSI models described above for more accurate assessment of RV function and potential application in RV PVR/insertion surgery design and patch optimization.

Figures 21A, 21B, 21C:
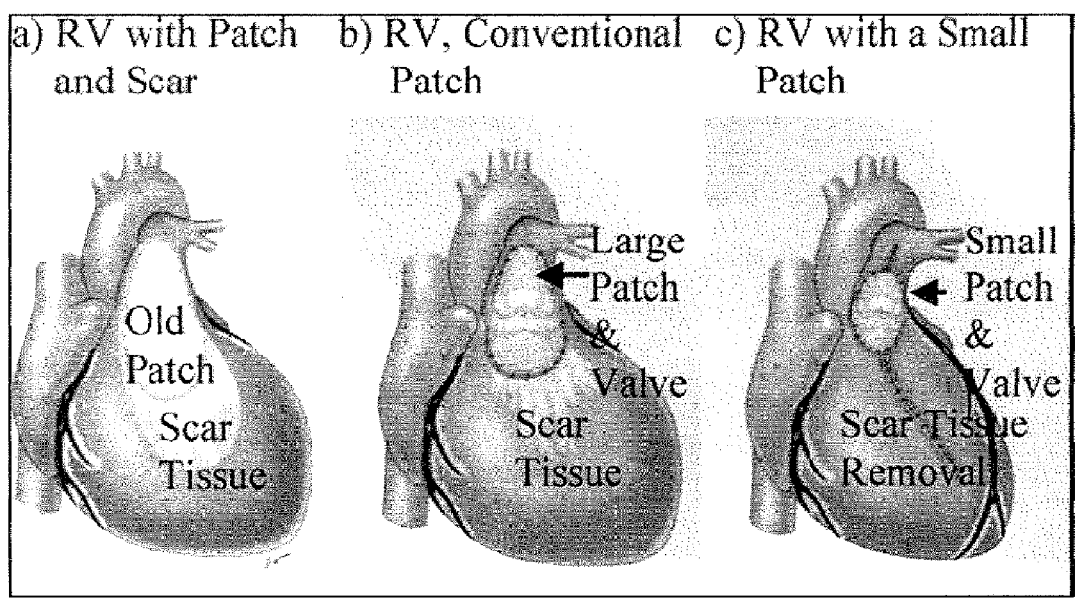
FIGS. 21(a)-21(c) are sketches of RV late after repair of tetralogy showing area of transannular patch plus thinning and scarring on the anterior surface of the RV (lighter gray area): (a) A diseased RV with old patch and scar tissue; (b) RV after pulmonary valve insertion (PVR) surgery with conventional patch; and (c) RV after PVR with scar removal and a smaller patch.
Figures 22A, 22B, 22C, 22D:
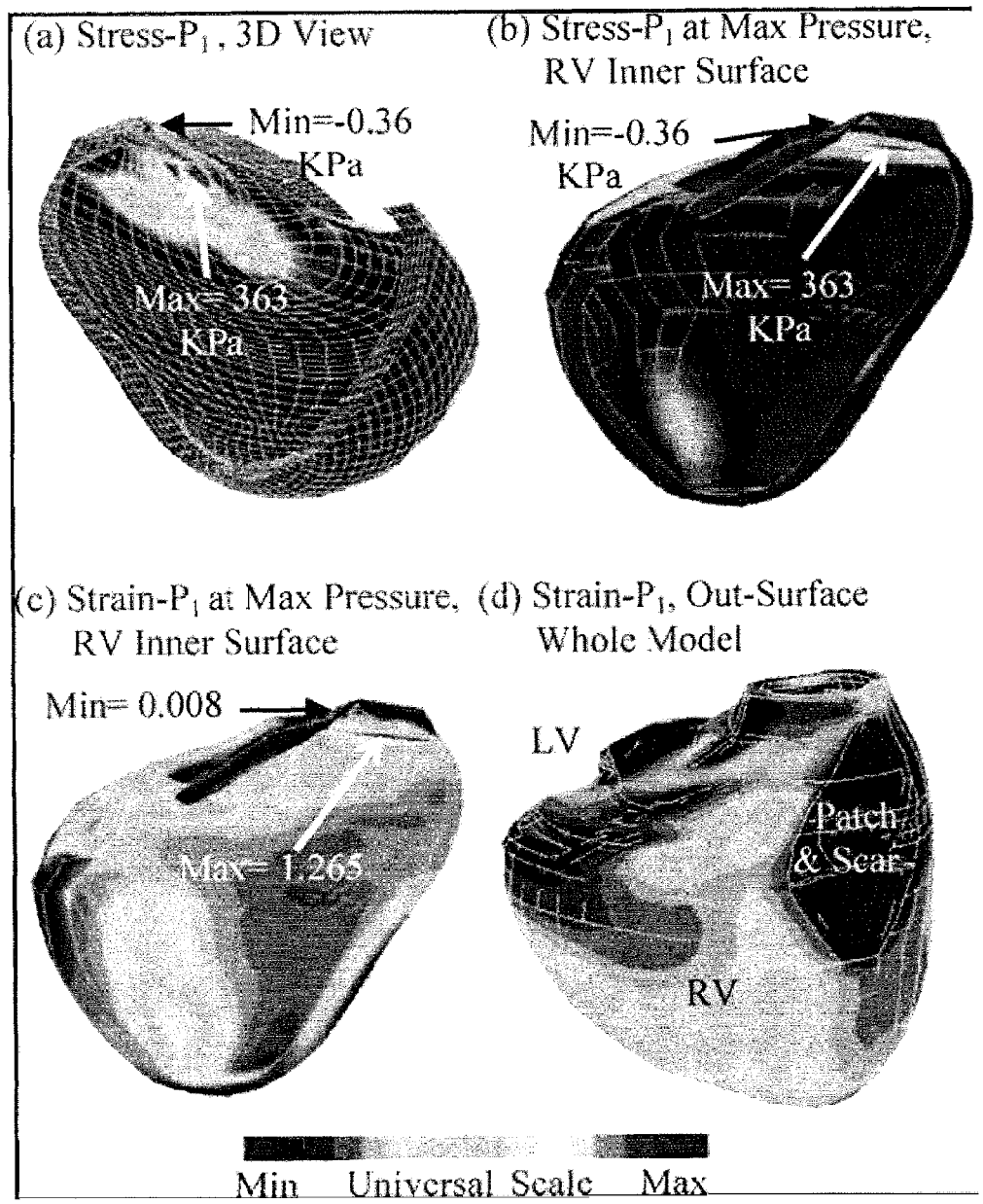
FIGS. 22(a)-22(d) are 3D views of Stress-$P_1$ and Strain-$P_1$ distributions in the RV, which may provide useful information for mechanical analysis and disease state assessment: (a) 3D view of Stress-$P_1$ under maximum pressure and position of the cut; (b) Stress-$P_1$ on the inner surface of RV under maximum pressure (horizontal flipped for better view); (c) Strain- $P_1$ on the inner surface of RV under maximum pressure; and (d) Strain-$P_1$ on the cut surface of the whole model.

The exact mechanism as how mechanical forces and conditions would contribute to RV failure or recovery is currently unknown due to lack of available clinical data and patient-specific computational models. The current surgical approach, which includes PVR/insertion, has yielded mixed results, with many of the patients seeing little if any improvement in RV function, while in others there is significant improvement (Tang et al., 2005, see above; and Yang, et al., 2007, see above; Therrien, J., Siu, S. C., and McLaughlin, P. R., 2000, "Pulmonary Valve Replacement in Adults Late After Repair of Tetralogy of Fallot: Are We Operating Too Late?," J. Am. Coll. Cardiol., 36, pp. 1670-1675; Vliegen et al., 2002, see above). The reason for the unpredictable results is the fact that the PVR surgery only addresses one mechanism for RV dysfunction and dilatation, namely pulmonary regurgitation. More radical surgical procedures, where scar tissue and even non-contracting segments of the RV muscle are removed (see FIGS. 2(a) and 21(a)-21(c)), are being performed (del Nido, et al., 2006, see above). FIGS. 21(a)-21(c) give sketches of a diseased RV with old patch and scar tissue and illustrations of the conventional and proposed surgical procedures. However there is currently no mechanism for predicting which patients will benefit from the various surgical options, and certainly no mechanism for tailoring the procedure to the individual patient with some confidence of the outcome.

Proposed herein is a novel surgical/modeling procedure to test the hypotheses that patient-specific image-based modeling can provide accurate information for assessment of RV function and that more aggressive scar removal using computer-aided surgery design with optimized post-operative RV morphology and patch design will lead to improved recovery of RV functions (del Nido, et al., 2006, see above). The detailed flow and stress/strain solutions from the computational model with FSIs can help better understand the mechanisms governing the disease development and the factors affecting the surgical outcome so that PVR procedure and patch design can be optimized.

In this example, passive and active 3D CMR-based RV/LV/Patch combination models which include a) FSIs, b) anisotropic material properties, c) two-layer construction with myocardial fiber orientation are introduced to provide accurate assessment for RV mechanical conditions and cardiac function. Active ventricle contraction was modeled by a material stiffening approach. Both passive and active models were validated by pre- and post-surgery CMR data and then used to assess and optimize RV remodeling surgical procedures and RV outflow patch design with the ultimate goal of improving recovery of RV function after surgery. Details are given below.

Data Acquisition Computational Models, and Solution Procedures

CMR data was first acquired and segmented to get RV/LV geometries. Valve and patch positions were determined with flow data, delayed enhancement CMR to delineate location and extent of scar/patch, and the intra-operative observations of Dr. del Nido. The computational mesh and finite element model were generated based on RV/LV geometries, valve locations and patch design. The complete LV/RV/Patch FSI model was solved by ADINA (ADINA R&D, Watertown, Mass., USA) using unstructured finite elements and the Newton-Raphson iteration method. Nonlinear incremental iterative procedures were used to handle fluid-structure interactions. ADINA is a well-tested commercial finite-element package and has been used by Tang et al. extensively to solve FSI models in the past 10 years (Tang et al., 2004, see above; Tang et al., 2005, see above; Yang et al., 2007, see above). More details for the solution methods can be found in Bathe, 1996 (see above) and Bathe, 2002 (see above).

Data was acquired as described in Example 4. FIGS. 13(a)-13(b) show one set of pre-operation CMR images from a patient and segmented contours, respectively. FIGS. 14(a), 14(b), 14(e) and 17(a)-17(c) show the stacked contours, RV/LV inner/outer surface plot, valve and patch positions, and two patch models modified from the pre-operative geometry for computational mechanical analysis. The patch models were constructed under guidance from Dr. del Nido with surgical limitations taken into consideration.

Solid model was established as described in Example 4.

The Passive Anisotropic Solid Model

Figure 24:
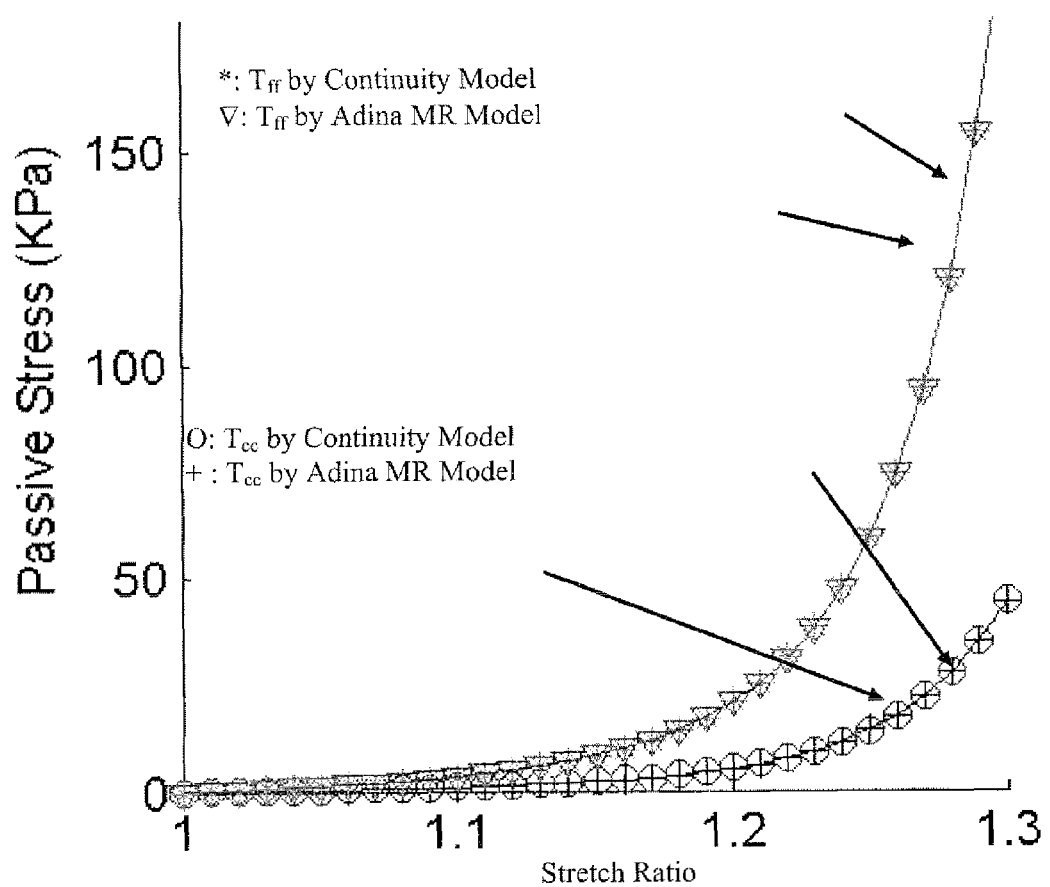
FIG. 24 is a graph showing that anisotropic Mooney-Rivlin Model matches well with the model in the Continuity package (McCulloch et al., 2007, see above). Parameters used for the Adina MR-model: $c_1$=0.351 KPa, $c_2$=0, $D_1$=0.0633 KPa, $D_2$=5.30, $K_1$=1.913 KPa, $K_2$=6.00.

The governing equations for the structure models, the strain energy function for the isotropic modified Mooney-Rivlin model were given in Examples 2 and 4. The strain energy function for the anisotropic modified Mooney-Rivlin model anisotropic model was obtained by adding an additional anisotropic term in Equation (14):

$$W=c_1(I_1-3)+c_2(I_2-3)+D1[\exp(D_2(I_1-3))-1]+ (K_1/2K_2)\exp[K_2(I_4-1)^2-1] \quad (20)$$

where $I_4=C_{ij}(n_f)_i(n_f)_j$, $C_{ij}$ is the Cauchy-Green deformation tensor, $n_f$ is the fiber direction, K1 and K2 are material constants (Holzapfel et al., 2000, see above). Parameter values in Holzapfel et al., 2000 (see above) can be chosen to fit the material models given in McCulloch, 2007 (see above) and McCulloch et al., 1992 (see above):

$$W=(C/2)(e^Q-1) \quad (21)$$

$$Q=b_1E^2_{ff}+b_2(E^2_{cc}+E^2_{rr}+E^2_{cr}+E^2_{rc})+b_3(E^2_{fc}+E^2_{cf}+E^2_{fr}+E^2_{rf}) \quad (22)$$

where $E_{ff}$ is fiber strain, $E_{cc}$ is cross-fiber in-plane strain, $E_{rr}$ is radial strain, and $E_{cr}$, $E_{fr}$ and $E_{fc}$ are the shear components in their respective coordinate planes, C, $b_1$, $b_2$, and $b_3$ are parameters to be chosen to fit experimental data. The 3D stress/strain relations can be obtained by finding various partial derivatives of the strain energy functions with respect to proper variables (strain/stretch components). Choosing $c_1$=0.351 KPa, $C_2$=0, $D_1$=0.0633 KPa, $D_2$=5.3, $K_1$=1.913 KPa, $K_2$=6.00 in Holzapfel et al., 2000 (see above). FIG. 24 shows the model agrees very well with the model given in McCulloch et al., 2007 (see above) and McCulloch et al., 1992 (see above). The patient-specific stress-stretch curves derived from the modified Mooney-Rivlin models fitting CMR-measured data are given by FIGS. 25(a)-25(b).

Active Anisotropic Material Model

Figure 25A:
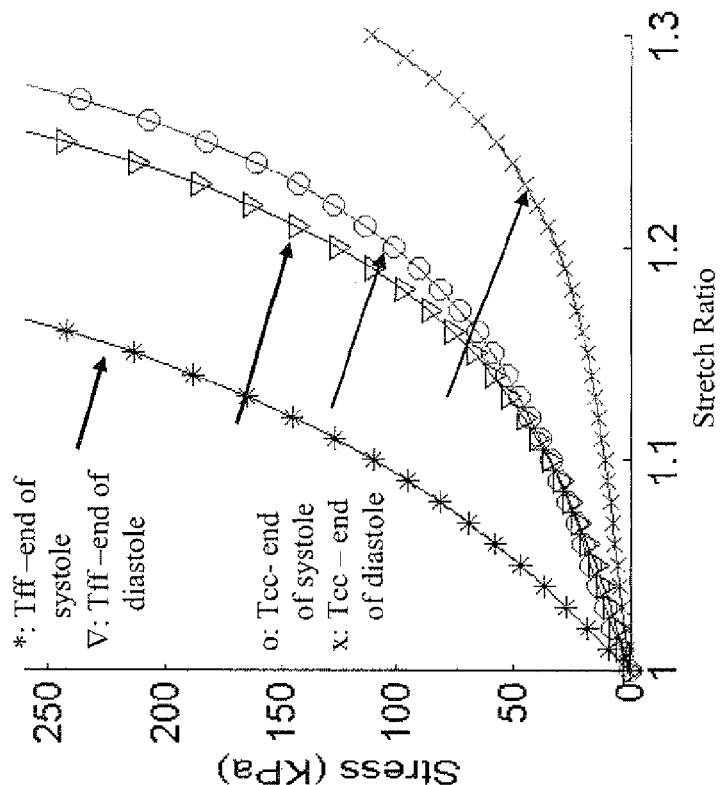
FIGS. 25(a)-25(b) are Stress-Stretch curves from isotropic and passive and active anisotropic models used herein. Model parameter values were selected to match CMR pressure-volume data: Isotropic RV tissue: $c_1$=7.36 KPa, $c_2$=0, $D_1$=2.88 KPa, $D_2$=4.0; Scar: $c_1$=73.6 KPa, $c_2$=0, $D_1$=28.8 KPa, $D_2$=4.0; Patch: $c_1$=147.2 KPa, $c_2$=0, $D_1$=57.6 KPa, $D_2$=4.0; Anisotropic Continuity model (Kuehne et al., 2004, see above) parameters: C=18.04 KPa, b1=8.79, b2=1.70, b3=0.774. (b) End-systolic and end-diastolic Tff and Tcc plots from proposed active patient-specific RV/LV model. End-systolic model parameters: C=72.16 KPa, b1=8.79, b2=1.70, b3=0.774; End-diastolic model parameters: C=22.55 KPa, b1=8.79, b2=1.70, b3=0.774.
Figure 25B:
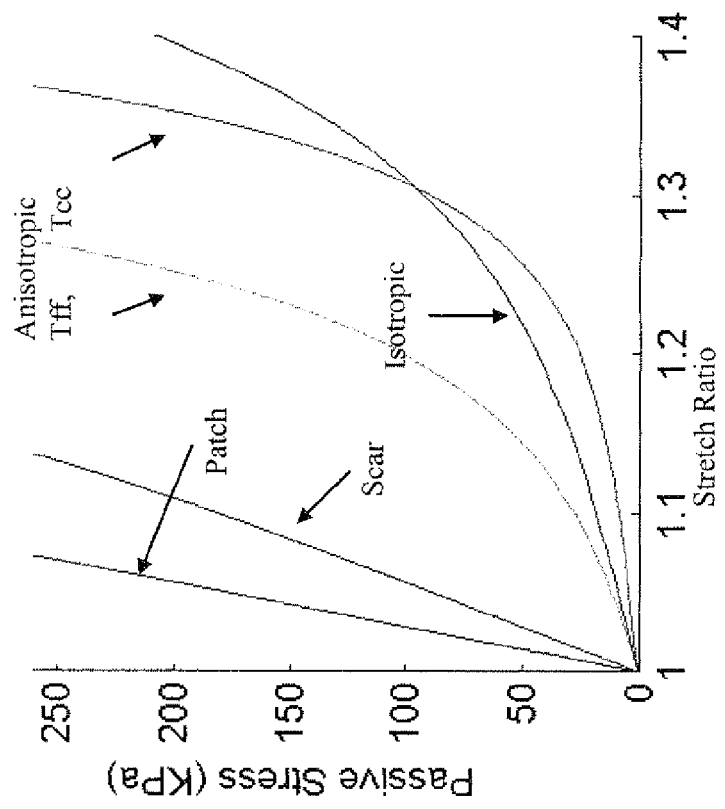
Figures 26A, 26B, 26C, 26D, 26E, 26F, 26G:
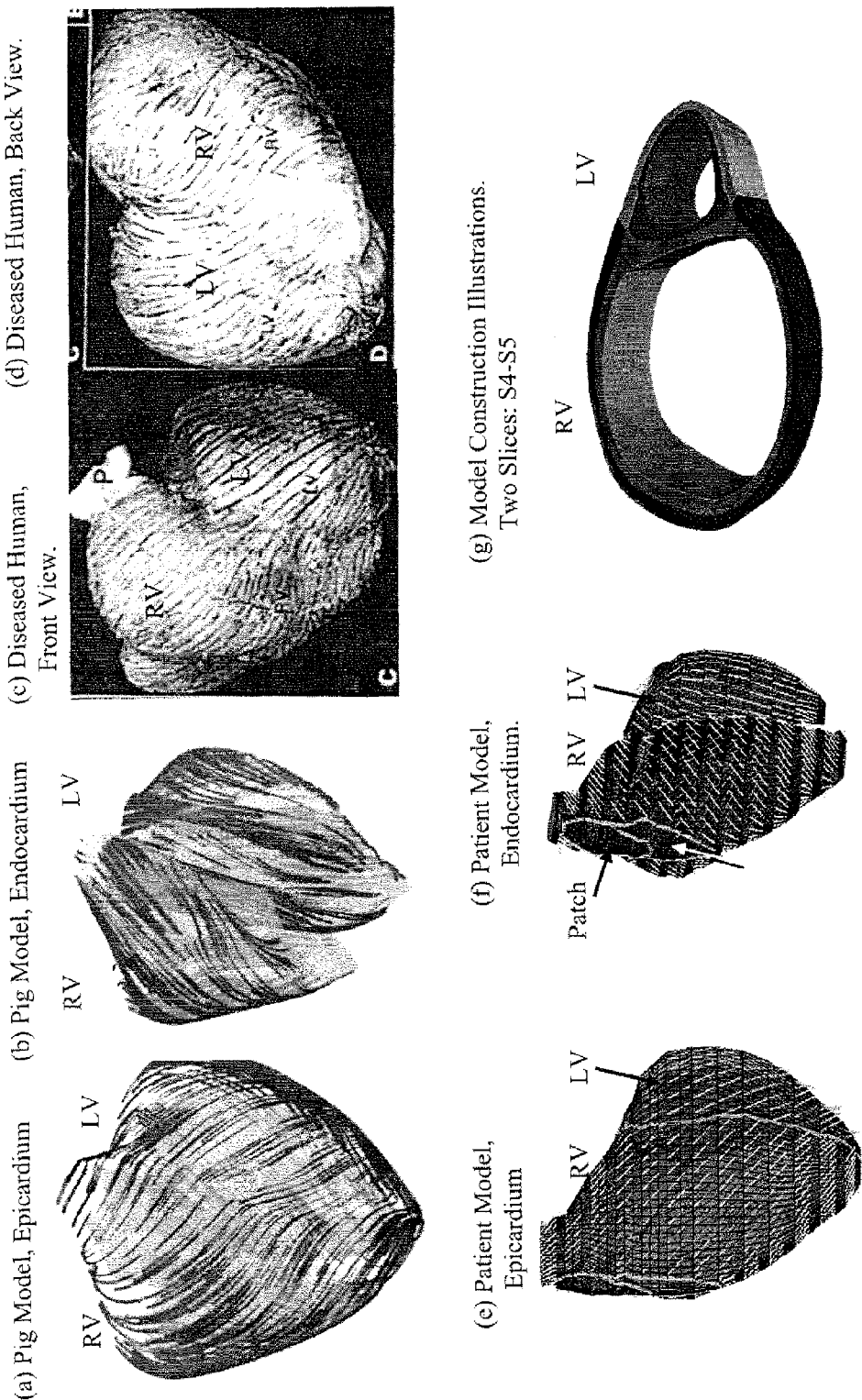
FIGS. 26(a)-26(g) are illustrations of fiber orientations from a pig model (Ref) and the patient-specific model according to the present invention: (a) on the epicardium, pig, (b) on the endocardial surfaces. LV fiber orientation is approximately −60° (relative to the circumferential direction) at the epicardium, and +80° at the endocardium. (c)-(d) Human ventricle fiber orientation from a patient; (e)-(f) Fiber orientation from the proposed RV/LV model based on patient-specific RV/LV morphologies. RV fiber orientation was set −45° at the epicardium, and +40° at the endocardium. The angles can be adjusted to fit patient-specific data. (g) Model construction illustrated using two slices.

Modeling active heart contraction is much harder because stress in a pumping human heart cannot be measured in vivo non-invasively (at least not with available technology in current practice). Heart expansion/contraction can be considered as combination of passive elastic expansion/contraction caused by blood pressure and active contraction/relaxation caused by fiber stiffening/relaxation. FSI plays an important role in the process. During the filling phase, increase of RV blood pressure causes passive elastic expansion of the ventricle, accompanied by RV fiber relaxation. In the ejection phase, RV material stiffens and leads to ejection; at the same time, RV blood pressure decrease also leads to (passive) elastic ventricle contraction. The stress/strain distributions (passive and active combined) are determined by mechanical conservation laws (Guccione, McCulloch and Waldman, 1991, see above; Guccione et al., 1997, see above) with proper boundary conditions and material constitutive laws. Since it is very hard to separate and measure the passive and active stresses/strains in clinical practice, time-dependent material stiffness parameters were specified to model RV tissue stiffening and active RV contraction. RV muscle fibers will contract/relax by following a time-dependent stiffening/relaxation material model. The time dependent material parameters in (Holzapfel et al., 2000, see above) are adjusted to match CMR-measured patient-specific pressure-volume values. FIGS. 25(a)-25(b) show the passive isotropic and anisotropic stress-stretch curves (FIG. 25(a)) and end diastolic/systolic stress-stretch curves for the active anisotropic model (FIG. 25(b)). The time-dependent stiffness parameters in Equation. (20) (each parameter in Bloomgarden et al., 1997 (see above) was a function of time) were numerically determined to match CMR measured RV volume curves.

Two-Layer Model with Fiber Orientation

As patient-specific fiber orientation data is not yet available in current practice, a two-layer RV/LV model and set fiber orientation angles using fiber angles given in Hunter, Pullan and Smaill, 2003 (see above; FIG. 26(a)-26(g)) were constructed. The angles can be adjusted in the model described herein easily volume by volume (the segment between two slices are divided into several blocks called "volumes" in ADINA so that proper mesh can be generated when patient-specific fiber orientation data becomes available (Sanchez-Quintana, D., R. Anderson, S. Y. Ho, (1996) Heart, 76, 280-286). FIGS. 26(a)-26(g) show fiber orientations on a patient-specific RV/LV model and a segment of the two-layer model between two slices. Fiber orientation data from Sanchez-Quintana et al., 1996 (see above) indicated that fiber orientations in human heart follow similar patterns as shown in FIGS. 26(a)-26(g).

Simulation Procedures

The equations described in the present invention give the complete FSI model, with proper initial and boundary flow, pressure and stress/strain conditions. The simulation cycle was performed as described in Example 4.

Results

Comparison of Passive Isotropic/Anisotropic and Active Anisotropic Models

Figures 27A, 27B, 27C, 27D, 27E:
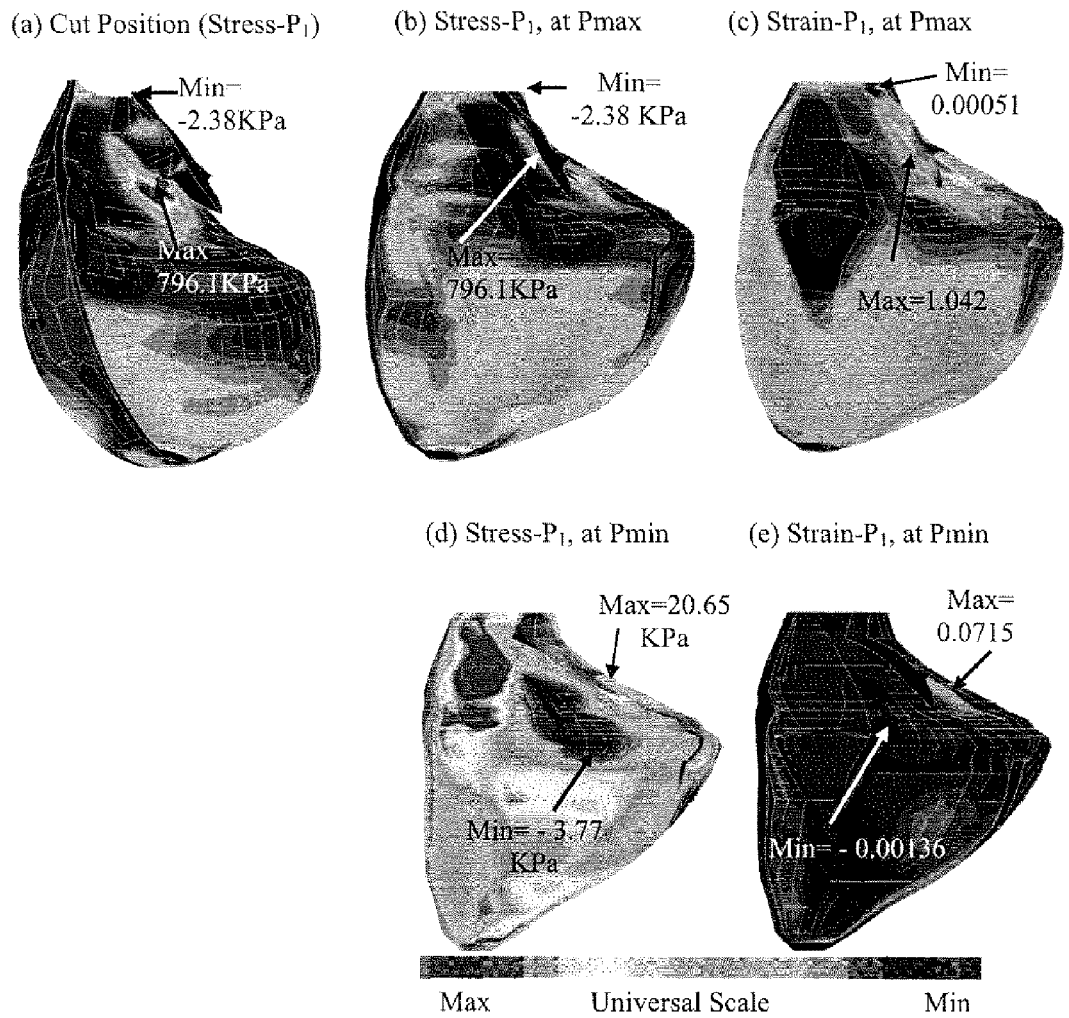
FIGS. 27(a)-27(e) are selected cut-surface and Stress-$P_1$ and Strain-$P_1$ plots from the active anisotropic model according to the present invention at Pmax (beginning of ejection phase) and Pmin (beginning of filling phase) conditions.

Nine fully-coupled FSI RV/LV combination models (the pre-operation model called M1, Patch Model 1 called M2 for conventional patch, Patch Model 2 called M3 with small patch and aggressive trimming, each with passive isotropic/anisotropic and active anisotropic material properties) were solved by ADINA to obtain full 3D flow, RV deformation and stress-strain distributions for detailed mechanical analysis and comparative studies. FIGS. 27(a)-27(e) give a cut-surface and selected stress/strain plots given by the active anisotropic pre-operation model corresponding to maximum and minimum pressure conditions. Maximum stress values were found to be closely related to RV curvature and wall thickness, less influenced by stiffness variations among RV tissue, scar and patch materials. Maximum principal strain (Strain-P1) distributions demonstrated closer link to stiffness changes, as shown by FIGS. 27(c) and 27(e).

Figure 28A:
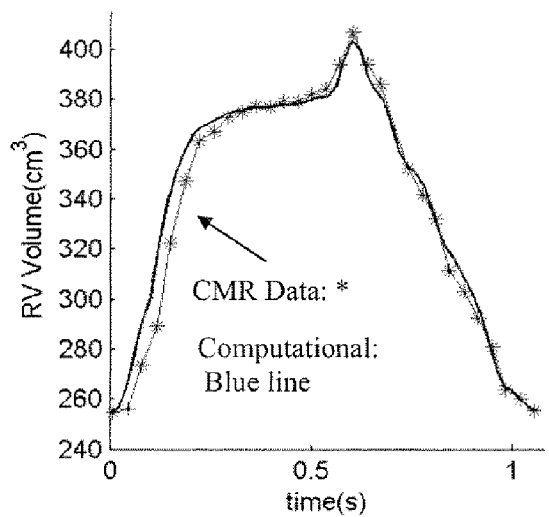
FIGS. 28(a)-28(b) are graphs showing good agreement (error margin <2% for the active model) between computed RV volumes from passive and active anisotropic pre-operation models compared with CMR recorded data. The active model has better agreement with CMR data because the material stiffness was adjusted for every time step to match with CMR volume data.
Figure 28B:
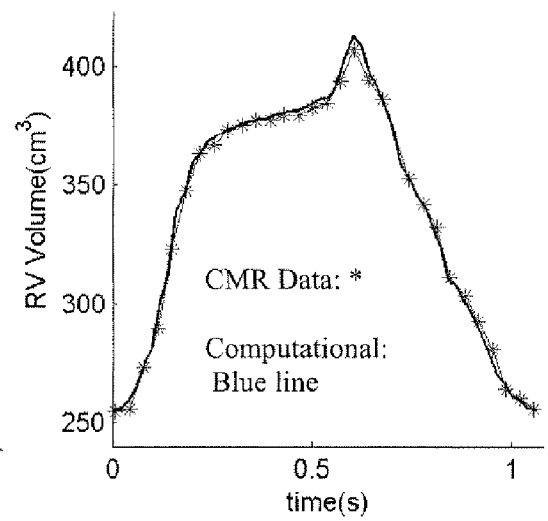
Figure 30A:
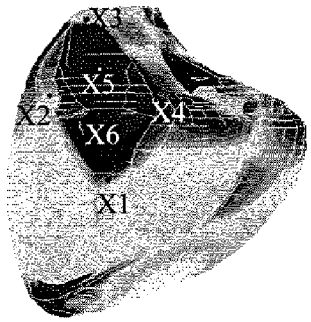
FIGS. 30(a)-30(d) are Strain-P1 plots and graphs of Stress-P1/Strain-P1 variations tracked at selected tracking points (marked on Strain-P1 plots) locations. Stress/strain levels in the patch area are considerably lower (>50% for stress, >20% for strain) from the pre-operation model to the other two models. Strain-P1 distributions from the three models were used to show locations of tracking sites. Selected tracking points and marking symbols in the plots: X1: *, just below the patch (or scar for M1); X2: x, just next to the left of the patch; X3: o, just above the patch; X4: +, just next to the right of the patch; X5: ∇, at the center of the patch; X6: Δ, just below the patch (this is for pre-op model only).
Figure 30B:
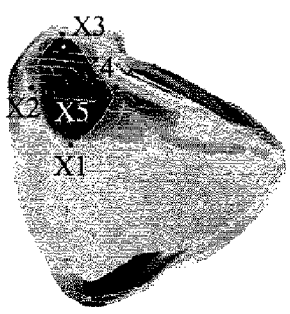
Figure 30C:
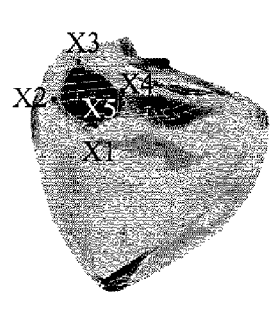
Figure 30D:
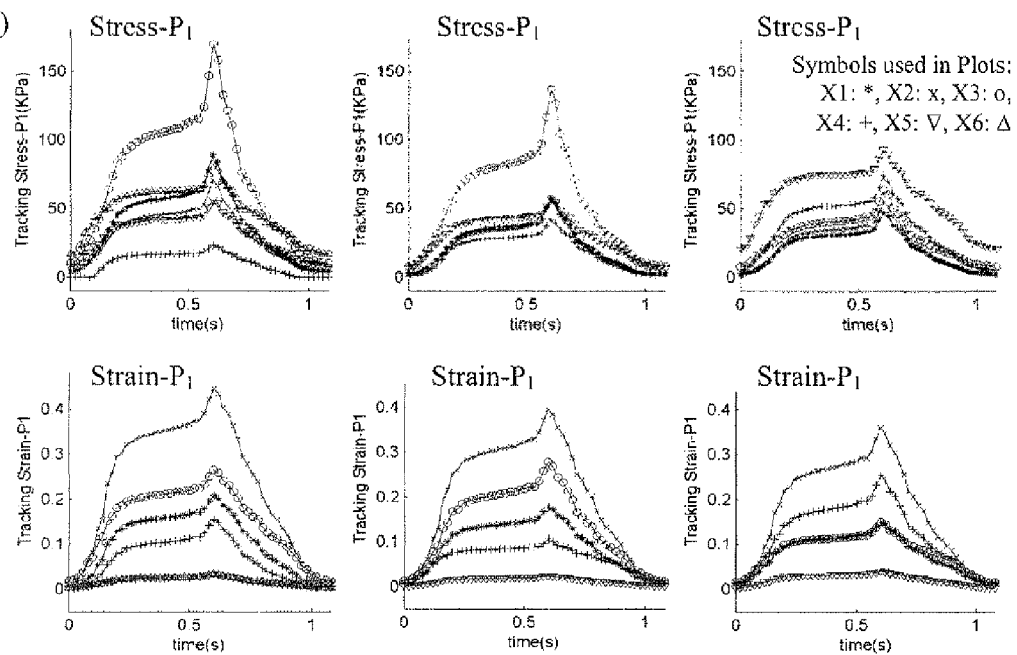

FIGS. 28(a)-28(b) show that the computed RV volumes from both passive and active anisotropic models agreed well with CMR data. The model with active contraction gave more accurate predictions (error margin <2% for the active model) because the material stiffness in the active model was adjusted for every time step to match with CMR volume data.

FIGS. 29(a)-29(f) give some interesting flow patterns and pressure band plots in the filling-ejection cycle from M2. At the beginning of the filling phase, pressure at the inlet is higher than the inside pressure, blood is pumped into the ventricle (FIGS. 29(a) and 29(d)). The filling continues until the inlet closes, the outlet opens, and the ejection phase begins (FIGS. 29(b) and 29(e)). As ejection continues, the ventricle contracts, more blood is pumped out of the ventricle (FIGS. 29(c) and 29(f)). Pressure contour plots on the cut-surface corresponding to the velocity plots are given showing that maximum pressure was found near the inlet at the beginning of the filling phase. During the ejection phase, minimum pressure was found at the outlet as expected.

Assessment of RV Cardiac Function and Patch Model Comparisons

Figure 20A:
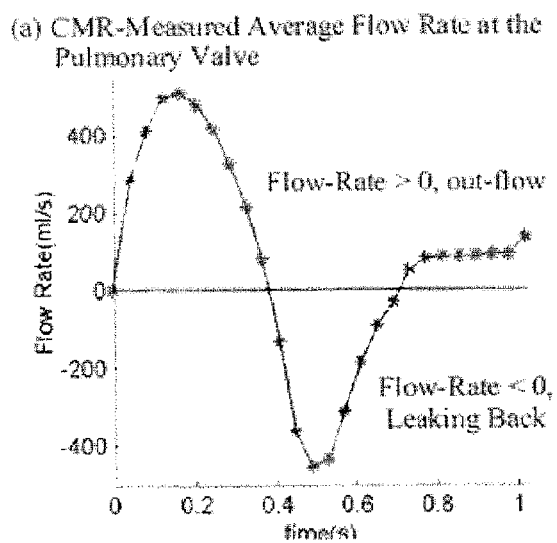
FIGS. 20(a)-20(b) are graphs showing CMR-measured averaged flow-rate and accumulated out-flow volume at the pulmonary valve for the pre-operation model, respectively.
Figure 20B:
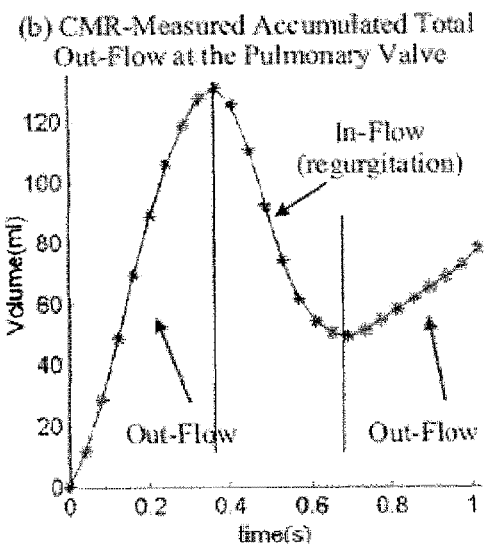

Based on the results and comparisons given in the previous section, the active anisotropic model was used to perform RV cardiac function assessment for the three patch models (M1, M2, and M3 as defined above) under consideration. RVEDV, RVESV, SV and EF values for M1, M2, and M3 are summarized in Table 3 which indicates that the proposed small patch model (M3) would provide about 11% improvement in EF, compared to the conventional patch model (M2). The fact that EF values for M1 and M2 were almost the same makes people wondering if the RV surgery brings any improvement for RV cardiac function. It should be noted that SV from the pre-op model is not a good measure of RV function because a considerable amount of blood leaks back through the pulmonary valve due to pulmonary regurgitation which is the reason for a PVI surgery. FIGS. 20(a)-20(b) give CMR-measured accumulated out-flow volume at the pulmonary valve for M1. With PR taken into consideration, the adjusted EF value for M1 is only 18.1%. The computer-predicted EF improvement of M2 and M3 over M1 were 104% and 126.5%, respectively, when PR is taken into consideration. This is an important finding since the implication is that valve insertion alone has a greater relative benefit (104%) compared to the remodeling (an additional 22.5%). This needs to be validated by clinical studies with both pre- and post-operation data.

TABLE 3

Stroke volume and ejection fraction comparisons for three models considered.

| Cases | Pre-Op Model (M1) Old (large) Patch + Scar | Pre-Op Model +Pulmonary Regurgitation | Patch Model 1 (M2) Conv. Large Patch | Patch Model 2 (M3) Small Patch + Trimming | CMR Data Post-Op actual data | Model 2 modified (M4) Using post-op data |
|---|---|---|---|---|---|---|
| RVEDV (ml) | 412.7 | | 256.9 | 208.7 | 188.3 | 118.28 |
| RVESV (ml) | 254.9 | | 162.1 | 123.2 | 115.0 | 115.65 |
| SV (ml) | 157.8 | 74.6 (outflow) | 94.9 | 85.5 | 73.3 | 72.63 |

TABLE 3-continued

Stroke volume and ejection fraction comparisons for three models considered.

| Cases | Pre-Op Model (M1) Old (large) Patch + Scar | Pre-Op Model +Pulmonary Regurgitation | Patch Model 1 (M2) Conv. Large Patch | Patch Model 2 (M3) Small Patch + Trimming | CMR Data Post-Op actual data | Model 2 modified (M4) Using post-op data |
|---|---|---|---|---|---|---|
| Ejection Fraction (%) | 38.2 | EF $PR_{adj}$: 18.1 | 36.9 | 21.0 | 38.9 | 38.6 |

M1: pre-operation model with scar + old patch;
M2: conventional patch;
M3: proposed small patch with aggressive trimming. Adjusted SY for M1 was obtained by including pulmonary regurgitation determined by CMR (FIGS. 20(a)-20(b)).
M4: small patch model with adjustment pressure condition to match post-operation CMR data.

Smaller Patch Leads to Reduced Stress Conditions in the Patch Area

To investigate mechanical conditions and stress/strain behaviors in the patch area, stress/strain values were tracked and FIGS. 30(a)-30(d) give Stress-P1 and Strain-P1 variations tracked at selected locations for the pre-operation model (M1), the conventional patch model (M2), and the small patch model (M3). The tracking results indicated that stress/strain levels around the patch were considerably lower from the small patch model compared to the conventional large patch model. Reduced stress/strain levels around the patch may be desirable for improved RV function and to prevent scarring of peri-patch myocardium, and should be taken into consideration in patch design process. This CST method is especially suitable for analyzing large 3D data sets to identify critical sites and indices related to the disease state under investigation (Tang et al., 2005, see above). The results also shows that stress conditions around the patch are far more sensitive to patch variations and may serve as better indicators for comparative analysis in patch design (size, shape and material properties) and optimization process.

Validation Using Pre- and Post-Operative Data

Figure 31A:
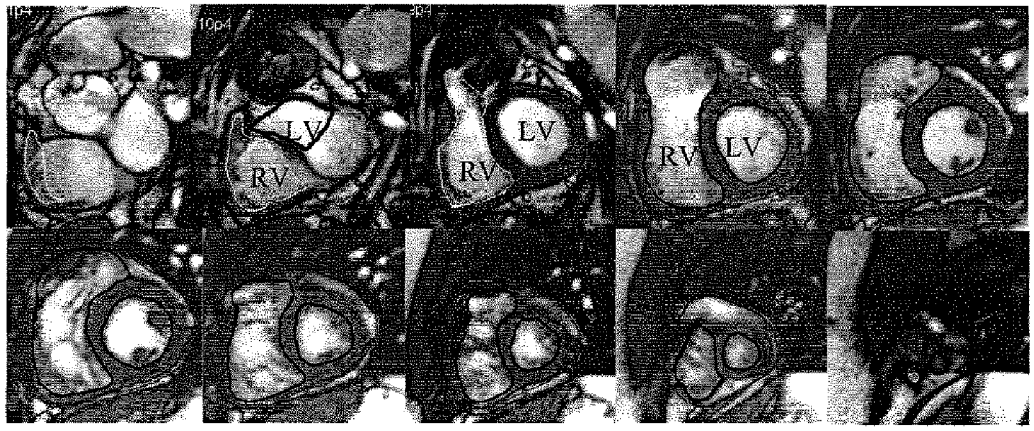
FIGS. 31(a)-31(c) show validation by post-operation data. (a) Post-operation CMR images; (b) Computational pre- and post-operation pressure conditions in RV; (c) Comparison between measured RV volume and two computational predictions. Blue line: volume using pre-operation pressure (CMR max volume 188.3 ml, predicted volume 204.9 ml, error margin 8.8%); black line: volume using adjusted pressure condition to match postoperation CMR RV volume (new predicted volume 188.28 ml, error <0.01%; error for the entire cardiac cycle <2%).
Figure 31B:
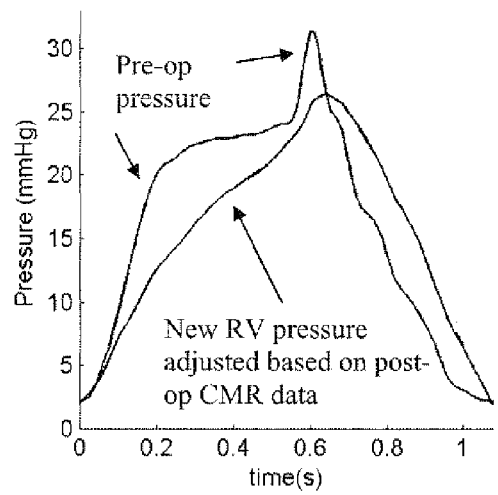
Figure 31C:
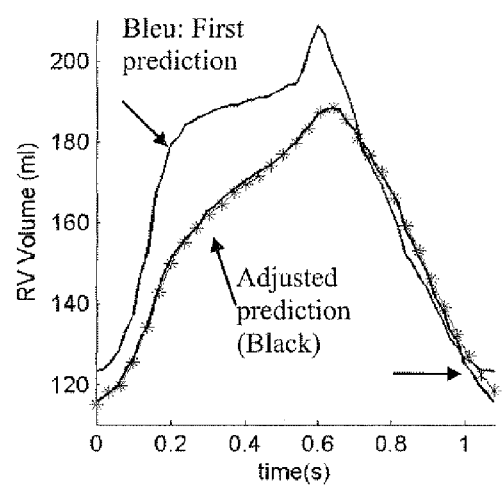

FIGS. 31(a)-31(c) give post-operation MR images of the same patient whose pre-operation data were used for demonstration. The CMR-measured and computer-predicted (patch Model 2) RV volume curves are given by FIG. 31(c), and the error margin is 8.8%. Noticing the differences in the volume profile and the over-all over-estimation by Patch Model 2, pressure condition and material parameters were adjusted and new predicted RV volume had much improved accuracy (new predicted maximum volume: 188.28 ml, error <0.01%; error for the entire cycle <2%). SV and EF values are listed in Table 3 to compare with those from other models. This modification technique can be applied to future cases so that the first-time prediction accuracy can be improved. Data obtained and experience learned can be applied to subsequent patient surgery design. The optimization process will improve as more pre- and post-operative data analysis and optimizations are completed.

Discussion

With the rapidly increasing number of late survivors of repair of ToF, surgical management of patients with right ventricular dysfunction has become a major clinical challenge. The wide variability in clinical status, extent of right ventricular dilatation, scarring, and dysfunction at the time of presentation has resulted in disparate surgical results with pulmonary valve insertion alone (Waien, S. A., P. P. Liu, B. L. Ross, W. G. Williams, G. D. Webb, P. R. McLaughlin. (1992) J Am Coll Cardiol. 20, 295-300). The proposed multi-disciplinary approach of integrating innovative computational modeling, surgical procedures and noninvasive CMR techniques has the potential for improved outcome of RV remodeling surgical procedures associated with pulmonary valve replacement surgery. For the first time, patient-specific 3D computational RV/LV/Patch combination models with FSIs and surgical procedure design will be developed to simulate blood flow and stress/strain in the right ventricle. Computational simulations can be used to supplement/replace empirical and often risky clinical experimentation, or even guide the design of new clinical trials to examine the efficiency and suitability of various reconstructive procedures in diseased hearts so that optimal design can be found. The proposed surgical procedures of RV remodeling can be tested and optimized by computational simulations before the surgeon actually operates on the patient.

Several improvements can be added to the models described herein in the future for better accuracy and applicability: a) Direct measurements of tissue mechanical properties will be very desirable for improved accuracy of models; b) Mechanical Valve mechanics and pulmonary regurgitation. While exact valve motion and mechanics are not included in the current model, the valve opening/closing can be controlled and adjusted to simulate PR. The model can be adjusted so that the outlet can be made partially open in the diastole period with proper pressure conditions specified to reach measured flow and RV volume variation data. c) Industrial patch materials can be used in the model for actual evaluations of different brands and product from different manufacturers. d) Active contraction model, as discussed in Example 4. Information obtained from animal models could be used as an approximate starting point (Guccione, Costa and McCulloch, 1995, see above; Guccione, McCulloch and Waldman, 1991, see above). It is expected that the SV and EF predictions by the current model and a heart model including active contractions will have the same accuracy.

In one embodiment of the present invention, there is provided a computer system that comprises: a) a data source containing data of a patient's heart; b) a modeler coupled to receive data from the data source, the modeler generating a patient-specific, three-dimensional, computational model of the heart based on the heart data; and c) a processor routine for computationally providing information about a certain cardiac function using the three-dimensional heart model and for applying computational, quantitative analysis of the cardiac function, wherein the quantitative analysis of the cardiac function provides an assessment for surgical options, optimizing surgical techniques, or predicting outcomes.

Figure 32:
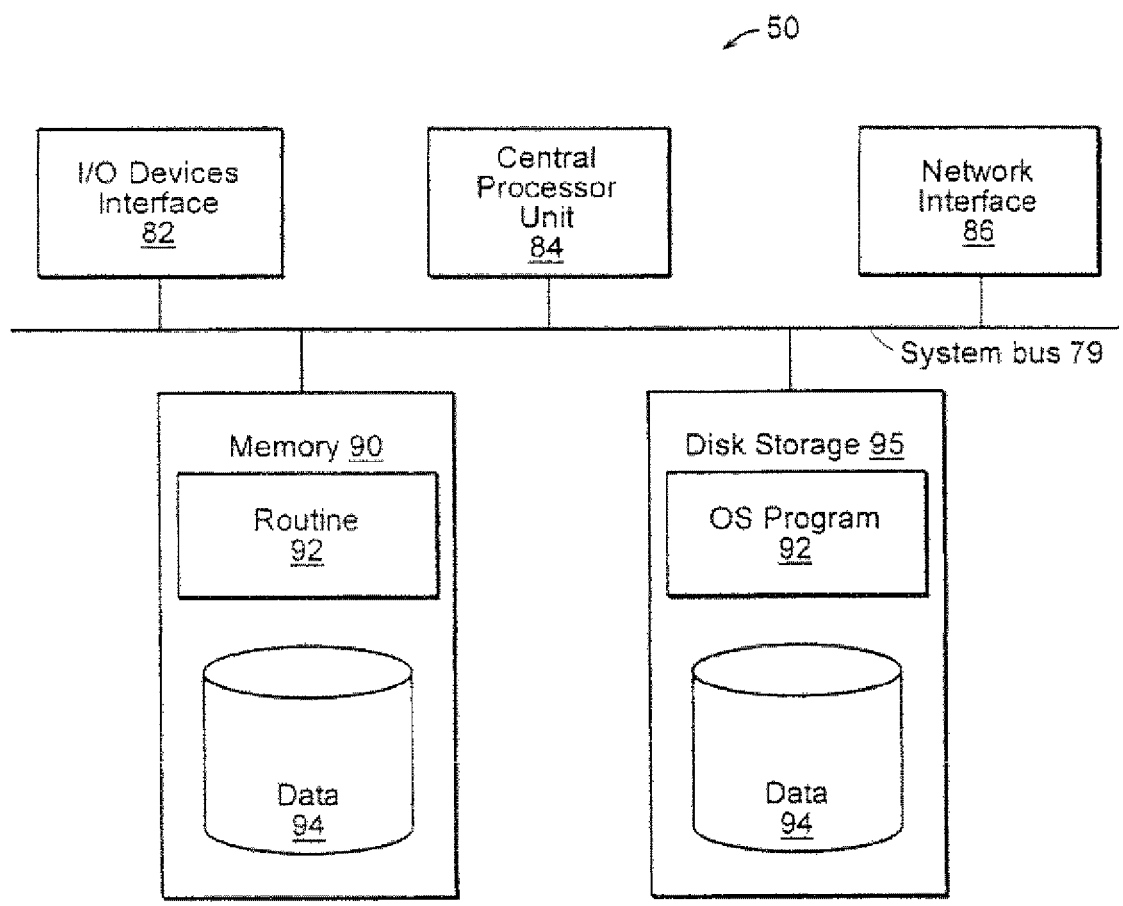
FIG. 32 is a block diagram of a computer or digital processing system in which embodiments of the present invention are deployed.

FIG. 32 is a diagram of the internal structure of a computer 50. The computer 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50. Network interface 86 allows the computer to connect to various other devices attached to a network (e.g., a wide area network, a local area network or global computer network). Memory 90 provides volatile storage for computer software instructions 92 and data 94 used to implement an embodiment of the present invention as described above. Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

The present invention may be implemented in a variety of computer architectures. The computer of FIG. 32 for purposes of illustration and not limitation of the present invention.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

While this invention has been particularly shown and described with references to example embodiments thereof, it will be understood by those skilled in the art that various changes in form and details may be made therein without departing from the scope of the invention encompassed by the appended claims.

What is claimed is:

1. A method for determining cardiac status, comprising:
for a given patient,
a) using a computer-based modeler, constructing a patient-specific, three-dimensional, computational model of the patient's heart, the model including fluid-structure interactions and right ventricle, left ventricle, and patch and scar tissues of the patient's heart, wherein the fluid-structure interactions include deformation of the patient's heart and are represented by a system of differential equations for solid mechanics and fluid mechanics;
by a processor, executing the constructed computational model, said executing generating a quantitative analysis of cardiac function, including assessment of ventricle volume based on a patient-specific simulation which simulates heart expansion and contraction by solving the differential equations, wherein the patient-specific simulation is based on ventricle pressure measured in the patient and includes mechanical stress/strain, flow velocity, shear stress and pressure; and
validating by the processor the model with pre-operative patient-specific data, including the measured ventricle pressure, prior to assessing surgical options to establish a validated model useable for surgical design,
the processor outputting to a user results of the generated quantitative analysis.

2. The method of claim 1, wherein the step of constructing comprises basing the model on patient-specific data including one or more of the data from ventricle morphology, cardiac motion, blood flow, material properties and pressure and volume conditions.

3. The method of claim 2, further comprising providing one or more of the patient-specific data before constructing the model.

4. The method of claim 3, wherein the step of providing one or more of the patient-specific data comprises acquiring the one or more patient-specific data using cardiac magnetic resonance.

5. The method of claim 1, further comprising constructing a three-dimensional, computational model of a healthy heart to serve as baseline control.

6. The method of claim 1, wherein the model further includes right ventricle/left ventricle/patch/scar interactions.

7. The method of claim 1, wherein the model includes valve mechanics.

8. The method of claim 7, wherein the valve mechanics comprise one or both of flow and solid stress/strain results.

9. The method of claim 1, wherein the model includes pulmonary regurgitation.

10. The method of claim 1, wherein the model includes fiber orientation and single-, double-, or multiple-layer anisotropic models.

11. The method of claim 10, wherein the anisotropic models comprise one or both of passive and active anisotropic models.

12. The method of claim 1, wherein the model includes an active contraction model.

13. The method of claim 12, wherein the step of constructing comprises introducing an external force field which is tied to fiber structure and orientations, thereby adding the active contraction model.

14. The method of claim 1, further comprising assessing surgical options based on the validated model, wherein the validated model includes localized flow and stress/strain information.

15. The method of claim 14, wherein the step of assessing comprises computationally designing the surgical options.

16. The method of claim 14, further comprising constructing predictive models of post-operative outcome for one or more of the surgical options.

17. The method of claim 16, wherein the predictive models comprise one or more patch models.

18. The method of claim 16, further comprising performing surgery based on one or more of the surgical options.

19. The method of claim 18, further comprising providing post-surgery data and validating or adjusting the predictive models based on the post-surgery data.

20. A method of performing cardiac surgeries, comprising:
   a) for a given patient, providing a patient-specific, three-dimensional, computational model of the patient's heart, the model being generated by a computer-based modeler, and the model including fluid-structure interactions and right ventricle, left ventricle, and patch and scar tissues of the patient's heart, wherein the fluid-structure interactions include deformation of the patient's heart and are represented by a system of differential equations for solid mechanics and fluid mechanics;
   b) using a processor, executing the patient-specific, three-dimensional computational model, said executing resulting in a quantitative analysis of cardiac function specific to the patient, including assessment of ventricle volume based on a patient-specific simulation which simulates heart expansion and contraction by solving the differential equations, wherein the patient-specific simulation is based on ventricle pressure measured in the patient and includes mechanical stress/strain, flow velocity, shear stress and pressure, and said quantitative analysis provides respective assessments of surgical options based on the patient-specific, three-dimensional, computational model of the patient's heart;
   c) validating the model with pre-operative patient-specific data, including the measured ventricle pressure, prior to the respective assessments of the surgical options to establish a validated model useable for surgical design; and
   d) performing surgery based on the respective assessments of one or more of the surgical options.

21. A computer system, comprising:
   a) a data source containing data of a patient's heart;
   b) a modeler coupled to receive data from the data source, the modeler generating a patient-specific, three-dimensional, computational model of the patient's heart based on the heart data, the model including fluid-structure interactions and right ventricle, left ventricle, and patch and scar tissues of the patient's heart, wherein the fluid-structure interactions include deformation of the patient's heart and are represented by a system of differential equations for solid mechanics and fluid mechanics; and
   c) a processor routine for computationally providing information about a certain cardiac function using the three-dimensional heart model and for applying computational, quantitative analysis of the cardiac function, including assessment of ventricle volume based on a patient-specific simulation which simulates heart expansion and contraction by solving the differential equations, wherein the patient-specific simulation is based on ventricle pressure measured in the patient and includes mechanical stress/strain, flow velocity, shear stress and pressure, and wherein the quantitative analysis of the cardiac function provides an assessment for surgical options, optimizing surgical techniques, or predicting outcomes, the processor validating the model with pre-operative patient-specific data, including the measured ventricle pressure, prior to the assessment for surgical options to establish a validated model useable for surgical design.

22. The computer system of claim 21, wherein the heart data includes one or more patient-specific data comprising: ventricle morphology, cardiac motion, blood flow, material properties and pressure and volume conditions.

23. The computer system of claim 22, wherein the one or more patient-specific data are acquired using cardiac magnetic resonance.

24. The computer system of claim 21, wherein the model further includes right ventricle/left ventricle/patch/scar interactions.

25. The computer system of claim 21, wherein the model includes valve mechanics.

26. The computer system of claim 25, wherein the valve mechanics comprise one or both of flow and solid stress/strain results.

27. The computer system of claim 21, wherein the model includes pulmonary regurgitation.

28. The computer system of claim 21, wherein the model includes fiber orientation and single-, double-, or multiple-layer anisotropic models.

29. The computer system of claim 28, wherein the anisotropic models comprise one or both of passive and active anisotropic models.

30. The computer system of claim 21, wherein the model includes an active contraction model.

31. The computer system of claim 30, wherein the active contraction model is added by introducing an external force field which is tied to fiber structure and orientations.

* * * * *